(12) United States Patent
Shah et al.

(10) Patent No.: US 10,449,539 B2
(45) Date of Patent: Oct. 22, 2019

(54) IMMUNO HISTO CHEMISTRY TISSUE PROCESSING SYSTEM AND CARTRIDGE THEREFOR

(71) Applicant: Rushabh Instruments, Inc., Warrington, PA (US)

(72) Inventors: Preyas Shah, Warrington, PA (US); Sahil Shah, Warrington, PA (US); Eli Endres, Malvern, PA (US); Joseph Lessard, Horsham, PA (US)

(73) Assignee: RUSHABH INSTRUMENTS, INC., Warrington, PA (US)

( * ) Notice: Subject to any disclaimer, the term of this patent is extended or adjusted under 35 U.S.C. 154(b) by 340 days.

(21) Appl. No.: 15/237,768

(22) Filed: Aug. 16, 2016

(65) Prior Publication Data

US 2017/0058245 A1    Mar. 2, 2017

Related U.S. Application Data

(60) Provisional application No. 62/210,670, filed on Aug. 27, 2015.

(51) Int. Cl.
*G01N 1/00* (2006.01)
*B01L 3/00* (2006.01)
*G01N 1/31* (2006.01)

(52) U.S. Cl.
CPC .......... *B01L 3/50273* (2013.01); *G01N 1/312* (2013.01); *B01L 2300/0819* (2013.01); *B01L 2300/0822* (2013.01); *B01L 2300/0832* (2013.01); *B01L 2300/0867* (2013.01); *B01L 2400/0478* (2013.01)

(58) Field of Classification Search
CPC ....................................................... B01L 1/00
See application file for complete search history.

(56) References Cited

U.S. PATENT DOCUMENTS

| | | | | |
|---|---|---|---|---|
| 5,047,211 | A * | 9/1991 | Sloane, Jr. | ......... G01N 33/4905 422/73 |
| 8,703,070 | B1 * | 4/2014 | Parng | .................... B01L 3/5025 422/407 |
| 2009/0209752 | A1 * | 8/2009 | Peters | ................. B01F 13/0059 536/25.41 |

\* cited by examiner

*Primary Examiner* — Jyoti Nagpaul
(74) *Attorney, Agent, or Firm* — RatnerPrestia

(57) ABSTRACT

A fluid-containing cartridge for a tissue processing apparatus includes a body defining a plurality of discrete fluid passageways, and a plurality of fluid-containing wells that are disposed on the body, wherein each fluid passageway of the body defines a fluid path between one of the fluid-containing wells and a fluid exit port that is configured to dispense fluid onto a laboratory slide.

30 Claims, 32 Drawing Sheets

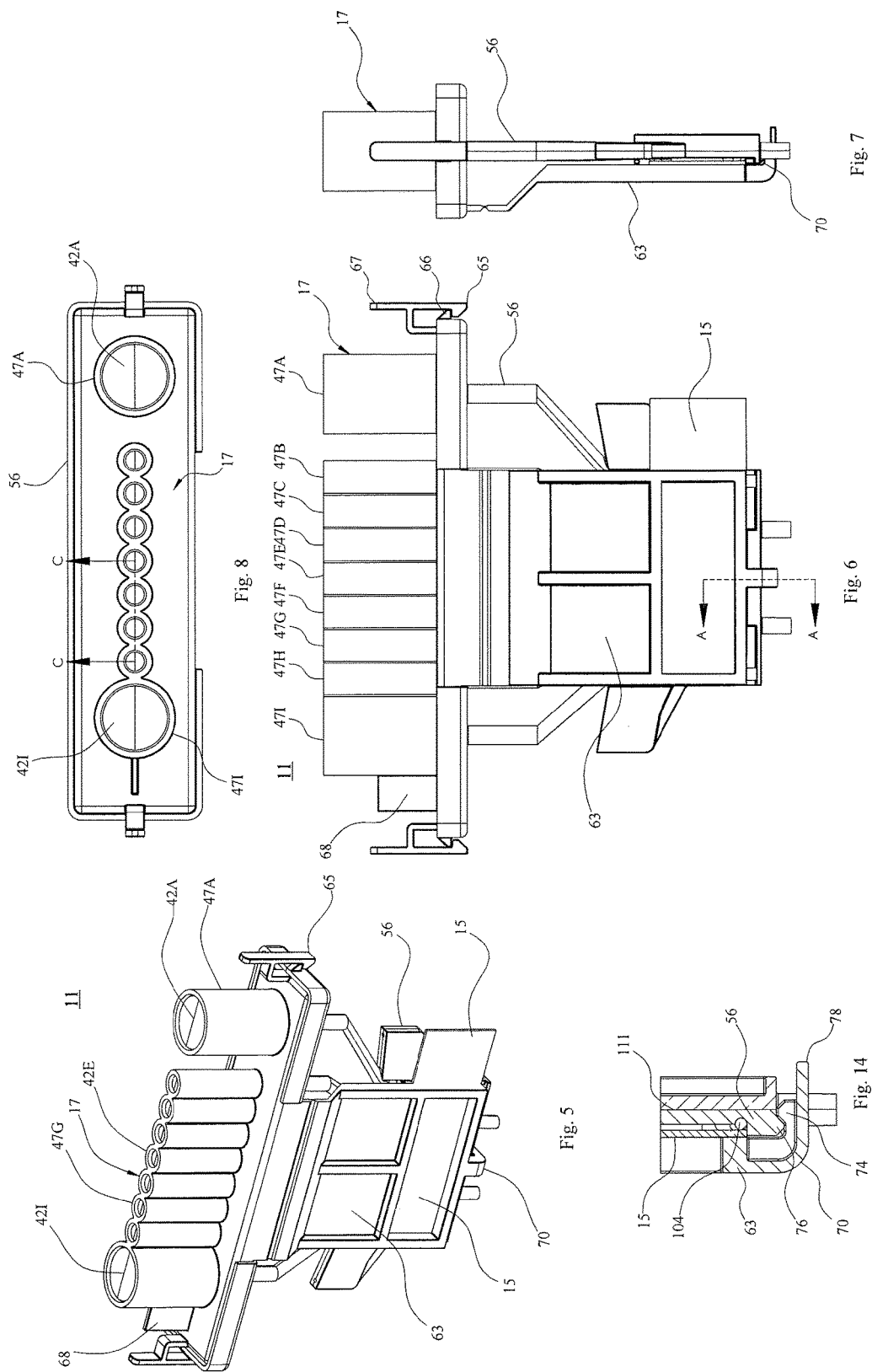

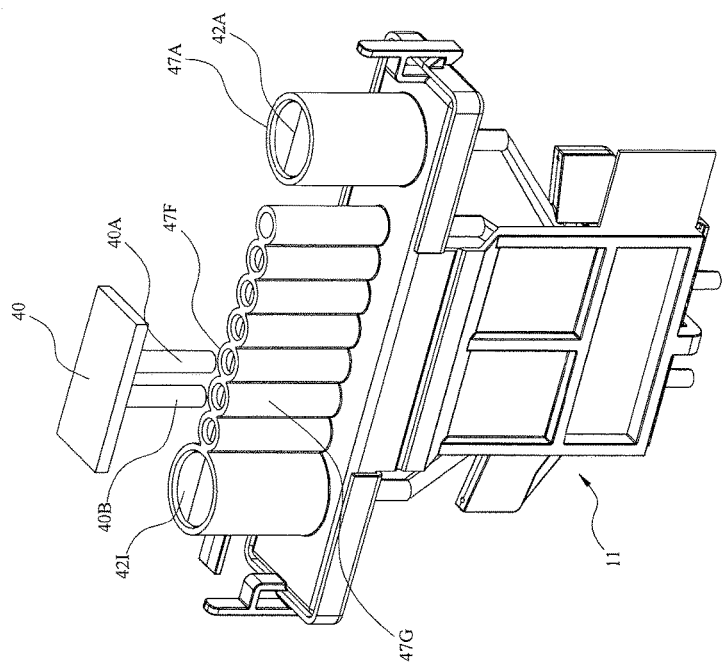
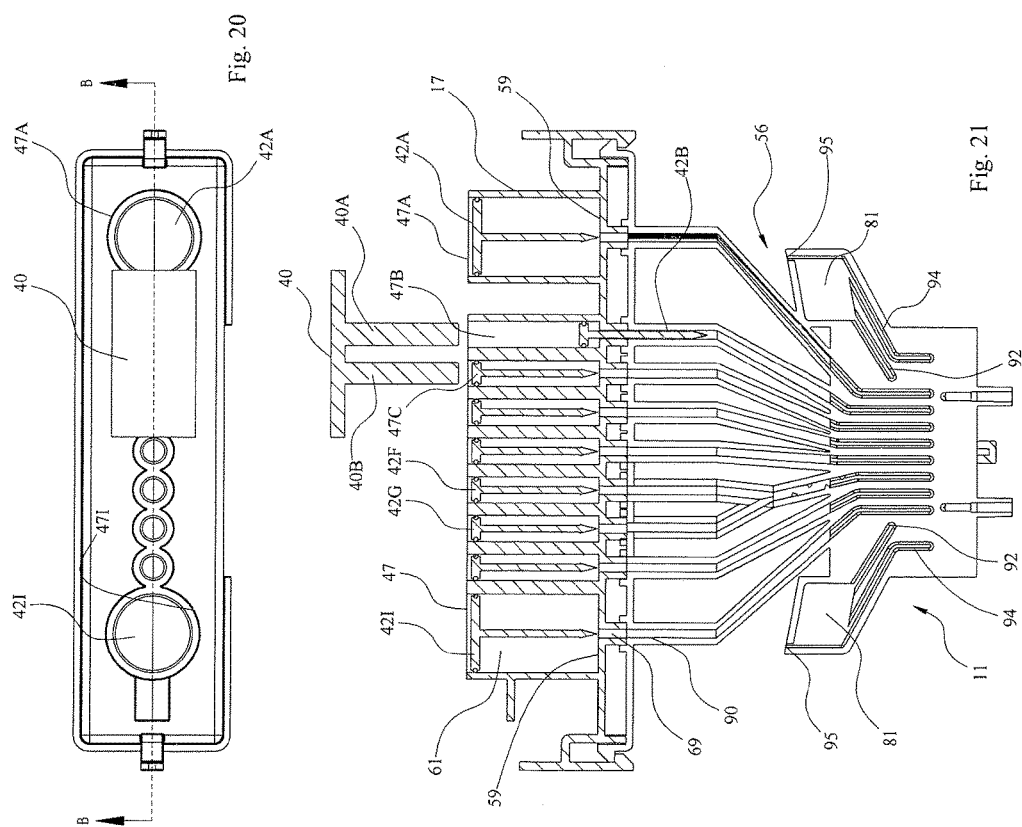

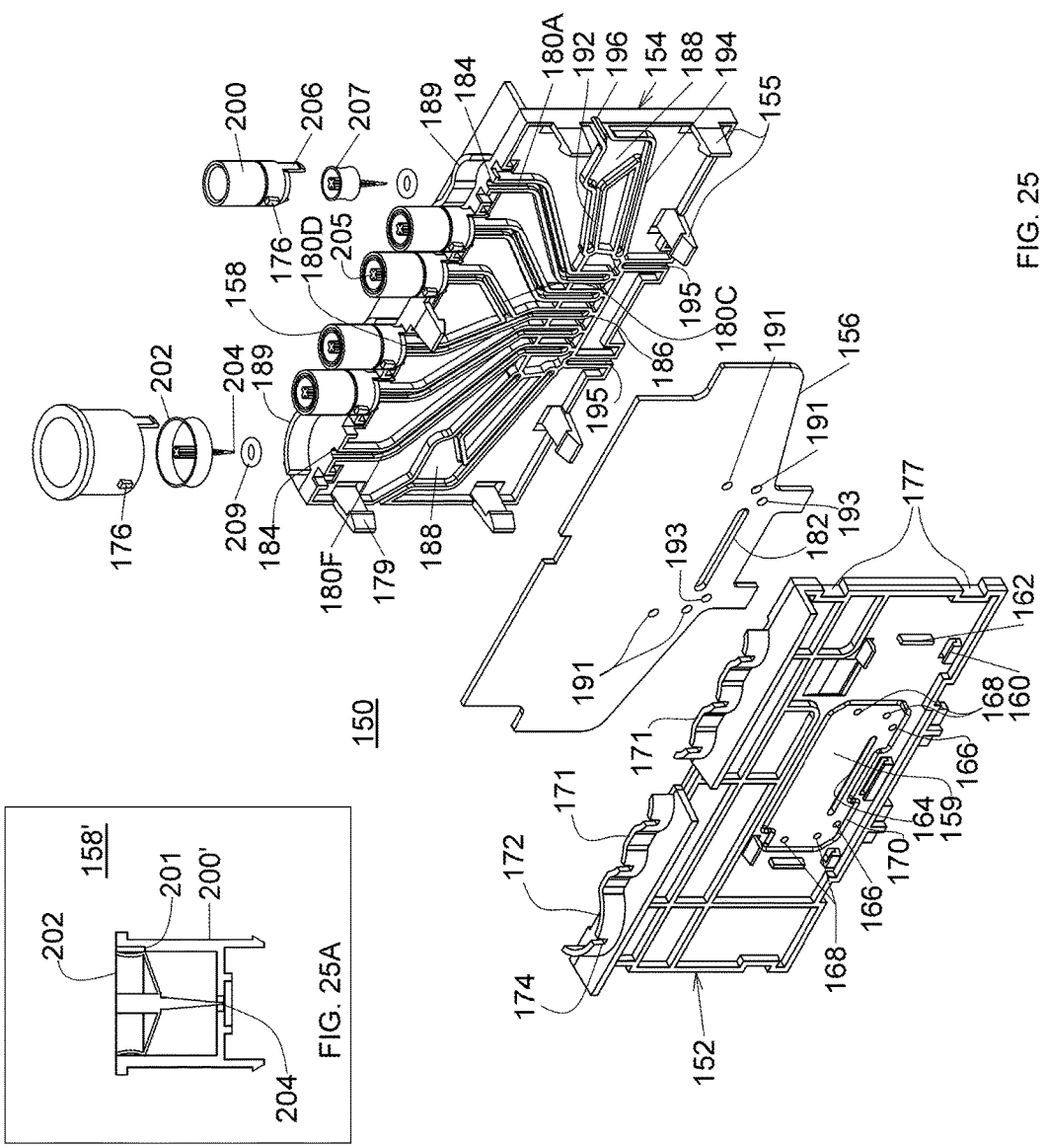

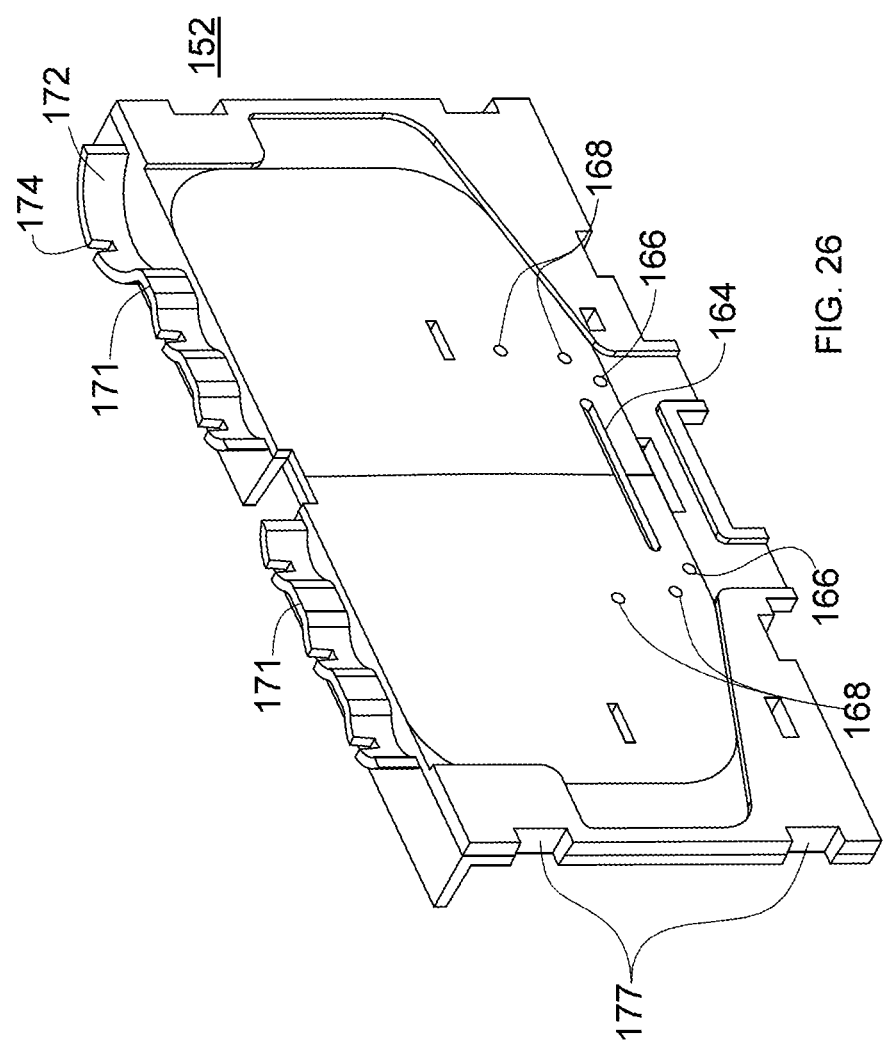

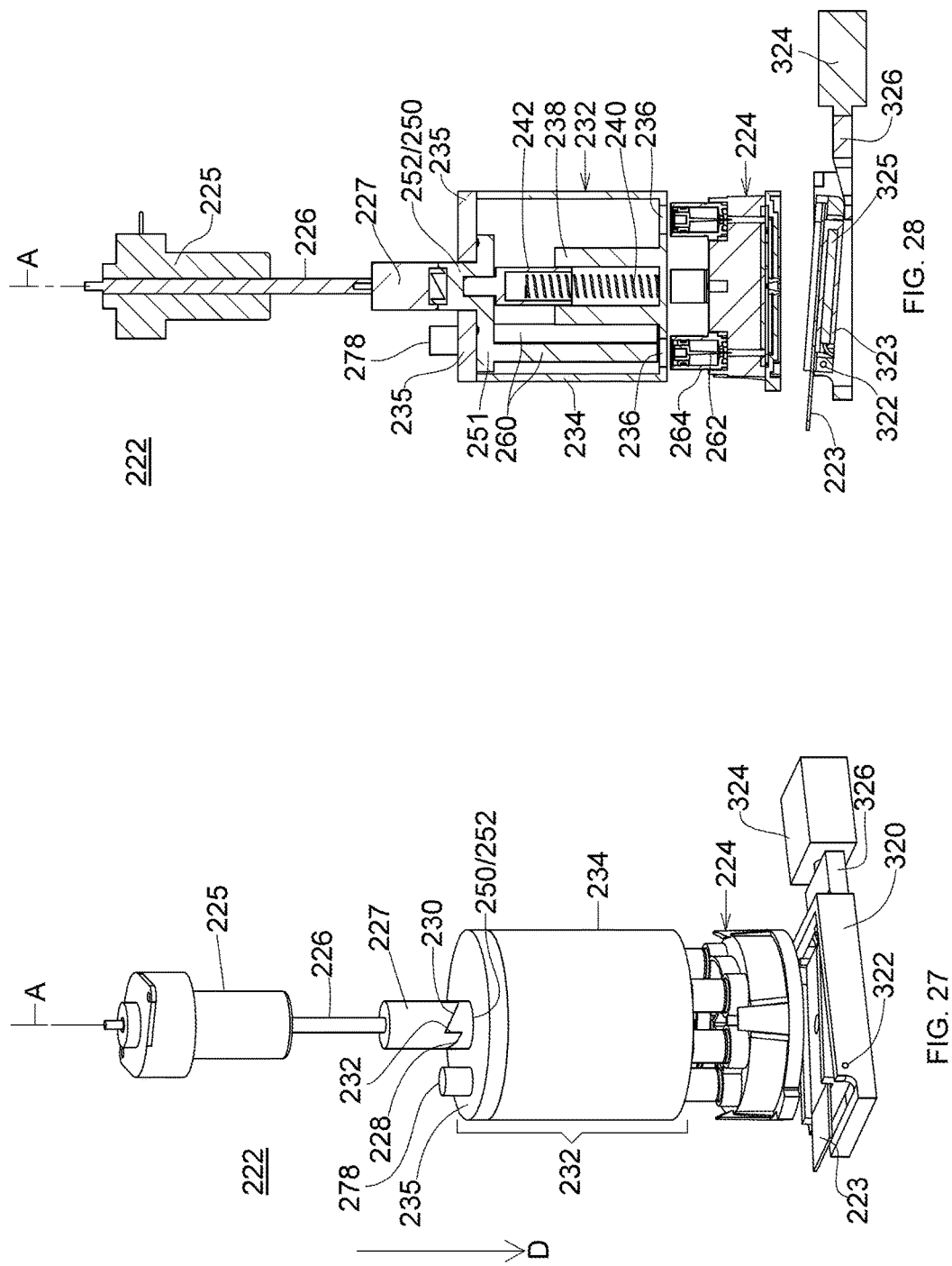

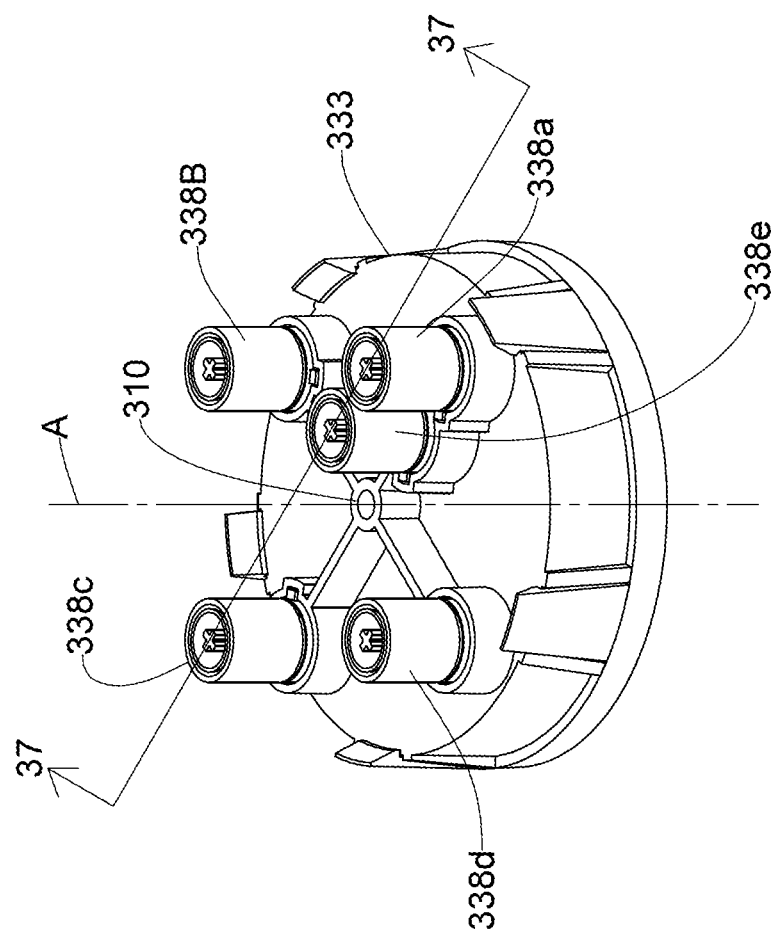

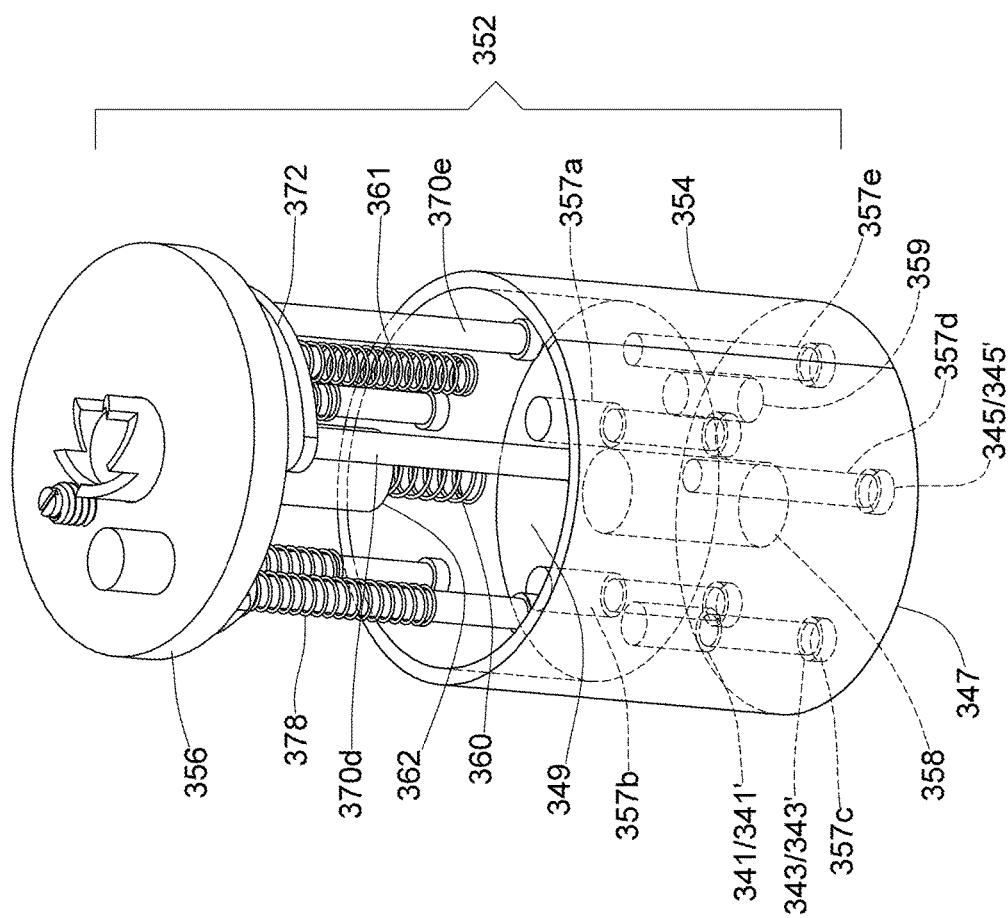

IMMUNO HISTO CHEMISTRY TISSUE PROCESSING SYSTEM AND CARTRIDGE THEREFOR

CROSS-REFERENCE TO RELATED APPLICATIONS

The present invention claims priority to U.S. Provisional Patent App. No. 62/210,670, filed Aug. 27, 2015, the contents of which are incorporated by reference herein in their entirety.

FIELD OF THE INVENTION

The present invention relates to an apparatus for processing tissue samples, and a slide cartridge for use with the apparatus.

BACKGROUND OF THE INVENTION

Laboratories routinely stain biological tissue specimens deposited on laboratory slides for subsequent pathologic examination to detect and/or monitor tissue abnormalities. An immuno histo chemistry (IHC) tissue processing apparatus is used to process samples for immuno-histological reaction staining. An IHC tissue processing system may also be referred to in the art as a slide stainer. Automated tissue processing systems allow batch processing of large numbers of slides containing tissue specimens for subsequent examination. In the course of a process, the tissue specimens are exposed to a series of well-defined processing steps that ultimately produces a properly processed specimen for examination. Automation of the process significantly reduces the time required to process tissue specimens, reduces the incidence of human error and allows processing parameters to be altered in an efficient manner. Improvements to tissue processing systems are continually sought in the interest of reliability, performance, speed and cost.

SUMMARY OF THE INVENTION

According to one aspect, a fluid-containing cartridge for a tissue processing apparatus comprises a body defining a plurality of discrete fluid passageways, and a plurality of fluid-containing wells disposed on the body, wherein each fluid passageway of the body defines a fluid path between one of the fluid-containing wells and a fluid exit port that is configured to dispense fluid onto a laboratory slide.

According to another aspect, a cartridge for a tissue processing apparatus comprises a body including a slide receiving area for accommodating a laboratory slide, a fluid passageway extending to the slide receiving area for delivering processing fluid to the slide receiving area, and, a condensation chamber separate from the slide receiving area for collecting vapor produced during processing of the laboratory slide and returning condensed vapors back to the slide processing area.

BRIEF DESCRIPTION OF THE DRAWINGS

The invention is best understood from the following detailed description when read in connection with the accompanying drawings. It is emphasized that, according to common practice, the various features of the drawings are shown schematically and may not be to scale. Included in the drawings are the following figures:

FIGS. 1, 2 and 3 depict a front elevation view, a top plan view, and a right side elevation view, respectively, of an IHC tissue processing system.

FIG. 5 depicts a perspective view of a cartridge assembly for use with the IHC tissue processing system of FIGS. 1-3.

FIGS. 6, 7, 8 and 9 depict a front elevation view, a right side elevation view, a top plan view and an exploded view, respectively, of the cartridge assembly of FIG. 5.

FIG. 14 is a cross-sectional view of the cartridge assembly of FIG. 6 taken along the lines A-A, revealing the clip attachment between the fluid pack and the cartridge frame.

FIG. 20 is a top plan view of the cartridge assembly of FIG. 18 and the pistons.

FIG. 21 is a cross-sectional view of the sub-assembly of FIG. 20 taken along the lines B-B, with the pistons of the IHC tissue processing system shown above two different pins of the cartridge.

FIG. 22 is a perspective view of the cartridge assembly and pistons of FIG. 18, with the pistons of the IHC tissue processing system shown positioned above two pins of the cartridge.

FIG. 25 is an exploded view of the cartridge assembly of FIG. 24.

FIG. 25A is a cross-sectional view of an alternative well for use with the cartridge assembly of FIG. 24.

FIG. 26 is a perspective view of the interior facing surface of the slide support frame of the cartridge assembly of FIG. 24.

FIG. 27 is a perspective view of another IHC tissue processing system.

FIG. 28 is a cross-sectional view of the IHC tissue processing system of FIG. 27.

FIG. 36 is a perspective view of the cartridge assembly of the IHC tissue processing system of FIG. 34.

FIG. 40 depicts an exploded view taken from the top side of the piston carriage of the IHC tissue processing system of FIG. 38, wherein the holes of the piston carriage are shown in phantom lines.

DETAILED DESCRIPTION OF THE INVENTION

Figure 1:
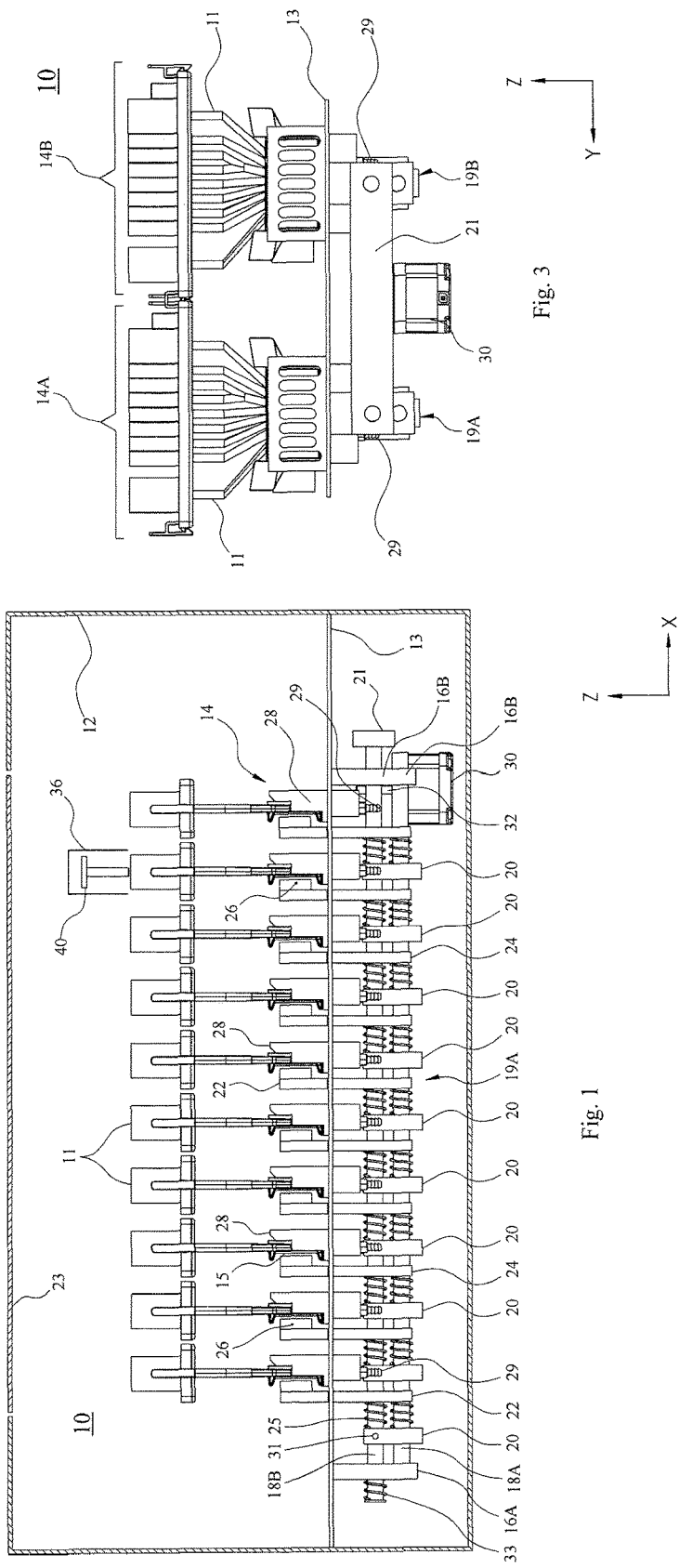

The invention will next be illustrated with reference to the figures. Such figures are intended to be illustrative rather than limiting and are included herewith to facilitate explanation of the present invention. In the drawing figures, like item numbers refer to like elements throughout. When a plurality of similar elements are present, a single reference numeral may be assigned to the plurality of similar elements with a capital letter designation referring to specific elements. When referring to the elements collectively or to a non-specific element, the letter designation may be omitted.

The drawing figures are not necessarily to scale and certain features of the invention may be shown exaggerated in scale or in somewhat schematic form in the interest of clarity and conciseness.

In the description, relative terms such as "horizontal," "vertical," "up,""down," "top" and "bottom" as well as derivatives thereof (e.g., "horizontally,""downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Figure 2:
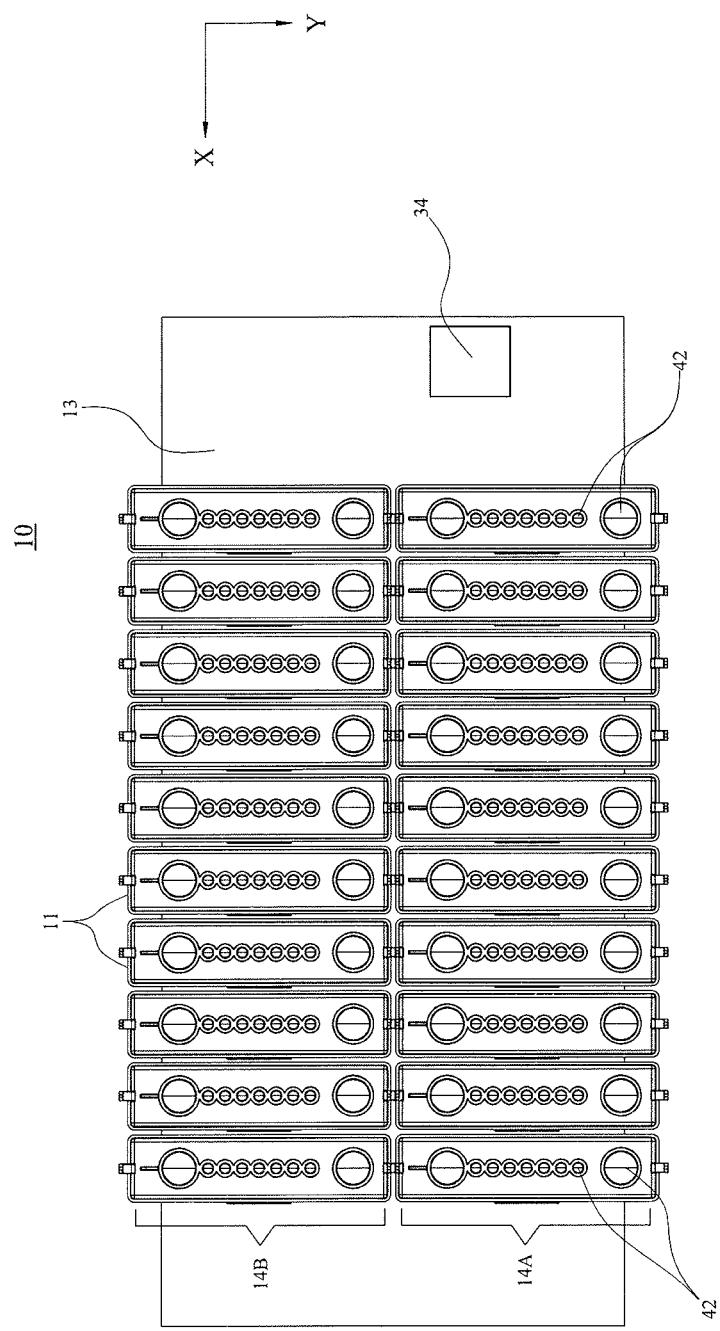

FIGS. 1, 2 and 3 depict a top plan view, a front elevation view and a right side elevation view, respectively, of an IHC tissue processing system 10 (referred to as tissue processing apparatus 10 hereinafter) for processing a plurality (twenty shown) of laboratory slides that are loaded in cartridge assemblies 11. Tissue processing apparatus 10 generally includes an enclosure 12, which is shown cut-away in FIG. 1 only, having an interior space for accommodating automated equipment for processing the slides. A baseplate 13 for supporting the automated equipment is mounted inside of enclosure 12.

A movable safety cover 23 may be either releasably or movably positioned on the top open end of enclosure 12 to provide selective access to the interior of tissue processing apparatus 10. Cover 23 prevents the operator from contacting any of the hot surfaces and moving parts inside of tissue processing apparatus 10 during operation. A sensor or switch (not shown) is connected to the enclosure 12 and/or cover 23 to sense the presence or absence of cover 23 on enclosure 12. Tissue processing apparatus 10 is configured to automatically deactivate if safety cover 23 has been opened or removed, as sensed by the aforementioned sensor or switch, during operation.

Figure 4:
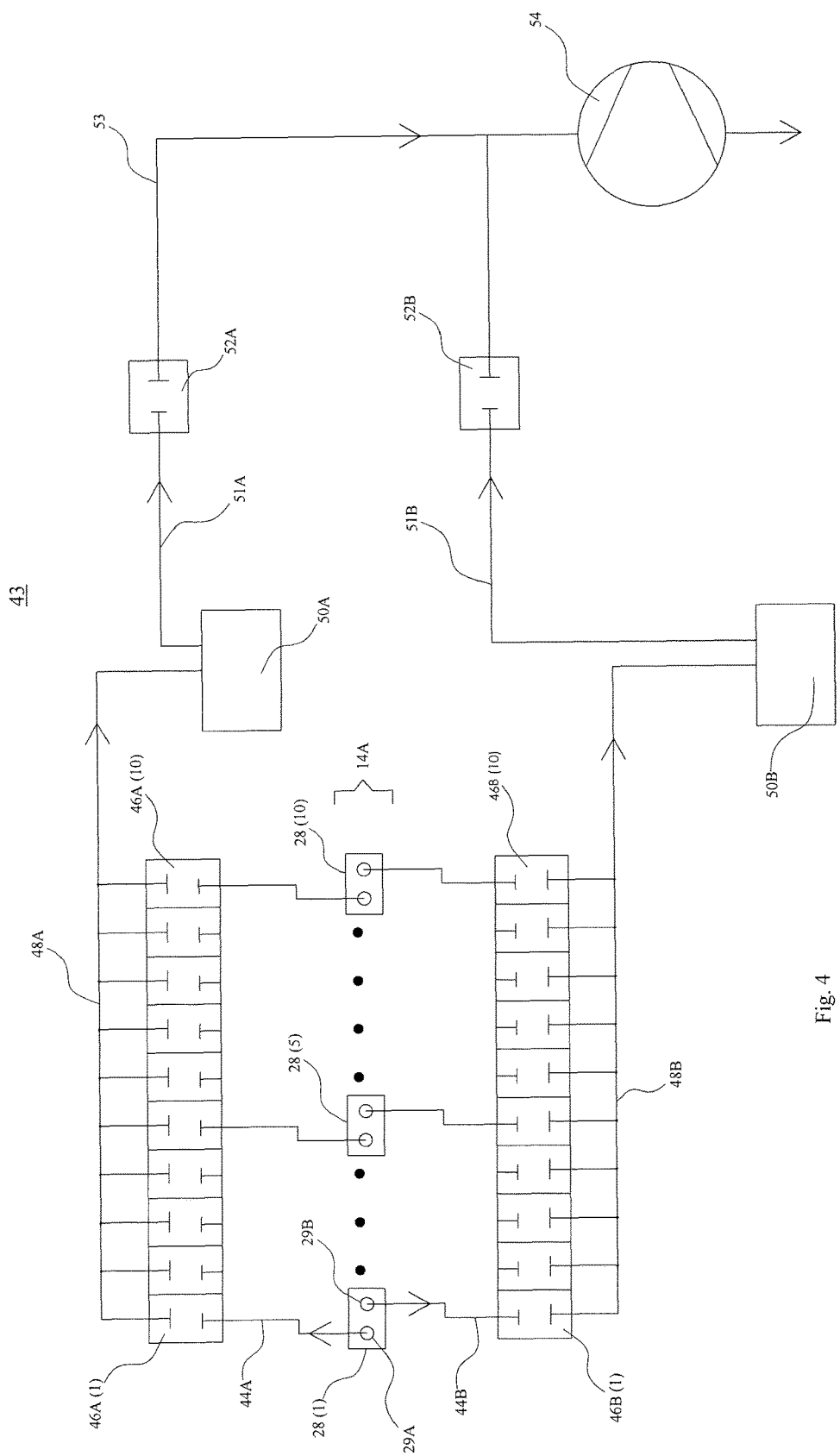
FIG. 4 is a block diagram of the fluid transport system of the IHC tissue processing system of FIGS. 1-3.

Tissue processing apparatus 10 includes a plurality of slide processing stations 14 (twenty shown) that are arranged into two separate rows 14A and 14B within the interior of enclosure 12. Tissue processing apparatus 10 may include any number of stations 14 that can be arranged in a variety of different ways (e.g., arranged in multiple rows or arranged in a circular fashion). Each slide processing station 14 defines a space in which a cartridge assembly 11 (shown in FIG. 5, for example) is removably positioned. A laboratory slide 15 is mounted to cartridge assembly 11, as shown in FIG. 4. During processing at each slide processing stations 14, a slide 15 is heated and exposed to multiple fluids within the fluid pack 17 of cartridge assembly 11. The heating step may be optional.

Two spring-loaded slide compression and heater assemblies 19A and 19B (referred to hereinafter either individually or collectively as assembly 19 or assemblies 19) are mounted to the underside of baseplate 13. Assemblies 19A and 19B are responsible for interacting (i.e., compressing and heating) with the laboratory slides 15 that are docked in rows 14A or 14B, respectively, of slide processing stations 14. More particularly, each assembly 19A and 19B is configured to selectively compress heating blocks 22 against the laboratory slides 15 that are docked in rows 14A or 14B, respectively, of slide processing stations 14. Assemblies 19 are mounted together by a plate 21 such that assemblies 19 move and operate simultaneously. Although only assembly 19A will be described hereinafter, it should be understood that assembly 19B is equivalent thereto and operates in the same manner.

Assembly 19A includes two stationary blocks 16A and 16B that are fixed to the underside of baseplate 13 (two stationary blocks 16 per row). Each stationary block 16A and 16B includes two holes in which rods 18A and 18B are positioned. Lower rod 18A is fixed to at least one of the stationary blocks 16A and 16B and cannot move, whereas upper rod 18B is capable of translating along the X-axis within the holes of stationary blocks 16A and 16B. A spring 33 is positioned between stationary block 16A and a flange on the free end of upper rod 18B to bias upper rod 18B to the left. Spring 33 is an optional feature of tissue processing apparatus 10 and may be omitted.

A series of ten rod blocks 20 are spaced apart along the length of rods 18. Each rod block 20 is fixed to upper rod 18B by a fastener 31 such that rod block 20 translates along with upper rod 18B. Rod blocks 20 are mounted on, but not fixed to, stationary lower rod 18A, and, thus, are capable of sliding over lower rod 18A.

A series of heating blocks 22 are positioned on both rods 18A and 18B. Each heating block 22 includes a base portion 24 having two holes through which rods 18A and 18B are positioned, and a heated portion 26 for heating a laboratory slide 15 against which heated portion 26 is positionable. Heated portion 26 may include an electrical heating element (not shown) or any other type of heating element that is known to those of ordinary skill in the art. Heating blocks 22 float on the rods 18A and 18B. In other words, heating blocks 22 are not fixed to either rod 18A or 18B, and, thus, are capable of sliding over both rods 18A and 18B.

Two springs 25 are mounted on respective rods 18A and 18B between adjacent rod blocks 20 and heating blocks 22. Springs 25 are configured to press heating blocks 22 against their respective slides 15 when rod blocks 20 and upper rod 18B are moved to the right, i.e., in a direction away from block 16A. Springs 25 provide enhanced thermal contact between the heating blocks 22 and their respective slides 15, as well as ensure that slides 15 do not separate from their cartridge assemblies 11 due to vapor pressures that may exist within cartridge assemblies 11 during processing of slides 15.

Preferably, each spring 25 is fixed to both blocks 20 and 22 between which it is sandwiched. This enables heating blocks 22 and springs 25 to move leftward and return to their original positions along with rod block 20 and so that cartridge assemblies 11 may be released from their respective stations 14. Alternatively, each spring 25 is not fixed to either one or both blocks 20 and 22.

A series of ten stationary cartridge receiving blocks 28 are fixedly mounted to base plate 13. Alternatively, cartridge receiving blocks 28 could also be fixed to stationary lower rod 18A, if so desired. Cartridge receiving blocks 28 and rod blocks 20 are not connected together. Each cartridge receiving block 28 includes an interior space or seat in which a single cartridge assembly 11 is removably seated. Each cartridge receiving block 28 further includes two separate and isolated fluid drain ports 29 (one shown) extending downward from a lower end surface thereof. Although not shown, each fluid drain port 29 is fluidly connected to a complimentary fluid port 86 (see FIG. 10) of a cartridge assembly 11 that is seated within the cartridge receiving block 28.

Spring-loaded slide compression and heater assemblies 19A and 19B are connected to each other such that they move together simultaneously. More particularly, the right-most end of upper sliding rod 18B of assembly 19A is connected to a bar 21, as shown. Similarly, the right-most end of upper sliding rod 18B of assembly 19B is also connected to the same bar 21. Thus, both assemblies 19A and 19B move concurrently with bar 21, and every block 20 and 22 moves along with bar 21.

A motor 30 having an output shaft in the form of a cam 32 is fixed to baseplate 13 or any other part of enclosure 12. Cam 32 is positioned adjacent the rear side of bar 21 (only the front side of bar 21 is shown in FIG. 3) for selectively translating bar 21 to the right against the bias of spring 33 attached to sliding rod 18B. Cam 32 is a conventional cam having a nose and a heel.

In another example, motor 30 may be omitted and replaced with a latch or other manually operated mechanism for moving bar 21 with respect to enclosure 12. In yet another example, the sliding rods 18B of the assemblies 19A and 19B may be disconnected and controlled by separate motors or latches. In still another example, both rods 18A and 18B could slide.

Referring now to the system for delivering the fluid to slides 15 of cartridges 11, one or more motorized and moveable carriages 36 (only one shown) are positioned above cartridges 11. Moveable carriage 36 is shown in FIG. 1 only, and is omitted from FIGS. 2 and 3.

Carriage 36 may be a conventional motorized X-Y-Z stage that is capable of moving along the X, Y and Z axes. The axes are shown in FIGS. 1-3. Tissue processing apparatus 10 may include only one carriage 36 that interacts with every slide cartridge assembly 11, as shown. Alternatively, tissue processing apparatus 10 may have multiple carriages 36 that are each positioned on top of one of the cartridge assemblies 11. Also, carriage 36 may be a component of tissue processing apparatus 10, as shown, or it may form part of another system that is attached to tissue processing apparatus 10.

A piston 40 is disposed on moveable carriage 36 and moves along with carriage 36. As will be described in greater detail with reference to FIGS. 18-22, piston 40 is operable to selectively depress pins 42 of cartridge assemblies 11 to deliver fluid, which is stored within wells 47, through cartridge assemblies 11 and onto slides 15. The passage of fluid through cartridge assembly 11 is described in greater detail with reference to FIG. 10. The fluid that passes through cartridge assemblies 11 is ultimately removed from the cartridge assemblies 11 by a fluid transport system 43, as will be described hereinafter.

FIG. 4 depicts a block diagram of a fluid transport system 43 for one row of processing stations 14A of tissue processing apparatus 10. Fluid transport system 43 is generally configured to transport waste fluid from cartridge assemblies 11 into at least two separate waste reservoirs for disposal. More particularly, as noted above, fluid drain ports 29A and 29B (referred to collectively as ports 29) of cartridge receiving blocks 28(1) through 28(10) (referred to collectively as blocks 28) are fluidly connected to the drain ports of cartridge assembly 11 (not shown in FIG. 4) such that fluid that is distributed through cartridge assembly 11 is ultimately delivered as waste fluid to fluid drain ports 29A and 29B of cartridge receiving blocks 28.

Fluid drain ports 29A and 29B of cartridge receiving blocks 28 are connected to a first end of conduits 44A and 44B, respectively. The second end of conduits 44A and 44B are connected to one port of solenoid-operated two-way valves 46A(1)-(10) and 46B(1)-(10), respectively. The other port of the solenoid-operated two-way valves 46A(1)-(10) and 46B(1)-(10) is connected to fluid manifolds 48A and 48B. Fluid manifolds 48A and 48B are fluidly connected to waste reservoirs 50A and 50B, respectively. One end of conduits 51A and 51B are fluidly connected to waste reservoirs 50A and 50B, and the other end of conduit 51A and 51B are fluidly connected to one port of solenoid-operated two-way valves 52A and 52B, respectively. The other port of solenoid-operated two-way valves 52A and 52B are fluidly connected to a fluid manifold 53, and fluid manifold 53 is connected to a vacuum pump 54.

Depending upon the open or closed state of valves 46A, 46B, 52A and 52B, pump 54 is configured to draw a vacuum through any one of the ports 29 of cartridge receiving blocks 28. For example, to dispose of waste fluid from port 29A of cartridge assembly 11 that is docked in block 28(1), valves 46A(1) and valve 52A are opened by a controller 34 of tissue processing apparatus 10. Pump 54 is then activated by controller 34 to draw a vacuum through block 28(1), thereby drawing waste fluid from port 29A of block 28(1) through conduit 44A, across open valve 46A(1), through manifold 48A and into waste reservoir 50A for disposal. As another example, to dispose of waste fluid from port 29B of cartridge assembly 11 that is docked in block 28(1), valves 46B(1) and valve 5BA are opened by controller 34 of tissue processing apparatus 10. Pump 54 is then activated by controller 34 to draw a vacuum through block 28(1), thereby siphoning waste fluid from port 29B of block 28(1) through conduit 44B, across open valve 46B(1), through manifold 48B and into waste reservoir 50B for disposal. Waste fluid may be drawn from blocks 28 simultaneously or in any particular desired order.

Two waste reservoirs 50A and 50B are provided to isolate one or more fluid waste streams from the other fluid waste streams. For example, the fluid in one well 47 of a fluid pack 47 may need to be recycled or disposed of in a special manner. Therefore, it is advantageous to provide at least two different waste reservoirs to isolate one or more waste fluids from the other fluids.

As noted above, FIG. 4 depicts a block diagram of a fluid transport system 43 for only one row of processing stations 14A of tissue processing apparatus 10. Although not shown, the other row of processing stations 14B of tissue processing apparatus 10 may be connected to waste reservoirs 50A and 50B in a similar manner.

As will be described in greater detail with reference to FIG. 10, pump 54 may also be used to draw a vacuum through any particular cartridge assembly 11 in order to reduce the temperature of a laboratory slide 15 mounted therein by forced convection of air through the interior of cartridge assembly 11.

The tubing, manifolds and valves of fluid transport system 43 described above may be positioned inside of enclosure 12 of tissue processing apparatus 10. Waste reservoirs 50A and 50B may be positioned outside of enclosure 12 of tissue processing apparatus 10 for ease of removal and replacement.

Pump 54, valves 46 and 52, the heating elements of heating blocks 22, motor 30 and motorized carriage 36 are connected to a computer controller 34 for controlling operation of those components of tissue processing apparatus 10. Tissue processing apparatus 10 may also include a keypad and/or display screen for manually entering parameters for controlling the operation of tissue processing apparatus 10. Tissue processing apparatus 10 may include a barcode reader for reading barcodes on slides 15 and/or cartridge assembly 11 before cartridge assembly 11 is loaded into tissue processing apparatus 10 for processing. The barcode reader may be attached to motorized carriage 36 (or another motorized X-Y-Z stage) so that it moves to each processing station 14 to scan the barcode on cartridge assembly 11 after one or more cartridge assemblies 11 are loaded into tissue processing apparatus 10 for processing.

Referring now to FIGS. 1-4, and according to one exemplary method of operating tissue processing apparatus 10, safety cover 23 is either opened or removed and the operator loads one or more cartridge assemblies 11 into their respective processing stations 14. A cartridge assembly 11 could be loaded into any one of the processing stations 14. Using the keypad on tissue processing apparatus 10, the operator can enter information regarding each slide cartridge assembly 11 that is to be processed by tissue processing apparatus 10. Cover 23 is then closed and processing of the slide cartridge assemblies 11 can begin.

Bar code information for each slide 15 and/or fluid pack 17 is then input into controller 34 of tissue processing apparatus 10 by a bar code reader. Bar code reader could be attached to motorized carriage 36, for example, and controller 34 could move the moveable carriage to each of the slides 15 and/or fluid packs 17 that are loaded into enclosure 12 and instruct the bar code reader to scan the individual bar codes. Alternatively, the operator could manually scan each bar code on the slide 15 and/or fluid pack 17 and upload that information to controller 34 using an external bar code reader either before or after cartridge assemblies 11 are loaded into their respective processing stations 14.

Once the bar code information is input into controller 34, tissue processing apparatus 10 heats one or more slides 15 that are loaded into processing stations 14 of tissue processing apparatus 10. More particularly, controller 34 activates motor 30 and cam 32 rotates. As cam 32 rotates, a nose of the lobe of cam 32 translates bar 21 to the right, i.e., away from block 16A, and against the force of spring 33. As noted above, as bar 21 moves to the right, sliding rod 18B, rod blocks 20 and heating blocks 22 also move to the right. Each heating block 22 eventually contacts the surface of its respective slide 15 as the heating blocks 22 move to the right. As each heating block 22 is moved further to the right toward its respective slide 15, springs 25 compress to dampen the force that is applied to the surface of slide 15 by heating block 22. Controller 34 activates heating portion 26 of heating block 22 to heat slide 15, according to a pre-defined slide processing protocol. The heating step may be omitted.

Either before, during or after the heating step, controller 34 activates motorized carriage 36 causing it to move along the X and/or Y directions so that piston 40 of carriage is positioned directly over one or more pins 42 (see FIG. 2) of a particular slide cartridge assembly 11. Controller 34 then causes motorized carriage 36 to move downward along the Z direction so that piston 40 of carriage depresses said one or more pins 42 of slide cartridge assembly 11, according to a pre-determined processing protocol, causing fluid to be delivered through cartridge assembly 11 onto a slide 15 that is mounted thereto. The intricate pathway of the fluid is described in greater detail below with respect to FIGS. 10-12. The slides 15 may or may not be heated by heating blocks 22 at this stage of the process.

The waste fluid (i.e., the fluid that has been delivered through cartridge assembly 11 and onto slide 15) may be removed from cartridge assembly 11, as will be described hereinafter, or, the waste fluid may remain in cartridge assembly 11 while further pins 42 are depressed thereby delivering more fluid through cartridge assembly 11.

After a predetermined time has elapsed, the waste fluid is ultimately removed from the cartridge assembly 11 by pump 54. The process for removing the waste fluid is described in the next paragraph. To dispose of waste fluid from the cartridge assembly 11 that is docked in block 28(1), for example, controller 34 opens valve 46A(1) and valve 52A. Controller 34 then activates pump 54 to draw a vacuum through the cartridge assembly that is docked in block 28(1), thereby siphoning waste fluid from cartridge assembly 11, through port 29A of block 28(1), into conduit 44A, across open valve 46A(1), through manifold 48A and into waste reservoir 50A for disposal. Port 29B of block 28(1) could also be accessed to dispose of waste fluid from the cartridge assembly 11 that is docked in block 28(1).

At this stage of the process, further pins 42 of a fluid pack 17 are depressed to deliver different processing fluids of fluid pack 17 through cartridge assembly 11 and onto slide 15. More particularly, controller 34 causes motorized carriage 36 to move upward along the Z direction so that piston 40 is again positioned above cartridge assembly 11 (see, e.g., FIG. 19). Controller 34 then activates motorized carriage 36 causing it to move along the X and/or Y directions so that piston 40 of carriage is positioned directly over a different pin 42 of slide cartridge assembly 11. Controller 34 then causes motorized carriage 36 to move along the Z direction so that piston 40 of carriage depresses said different pin 42 causing fluid to be delivered through cartridge assembly 11 to slide 15 that is mounted thereto. That waste fluid is then removed by pump 54 and disposed of in the waste reservoirs 50A and/or 50B, as described above. This process continues until all of the desired pins of a particular slide cartridge assembly 11 have been depressed, and the waste fluid has been removed from cartridge assembly 11, Referring back to FIGS. 1-3, once processing of slides 15 is complete, the cartridge assemblies 11 are ready to be released and removed from tissue processing apparatus 10. More particularly, controller 34 activates motor 30 to rotate cam 32 until the heel (not shown) of cam 32 is positioned closest to bar 21. As cam 32 rotates, the following components move to the left so that the heating blocks 22 separate from the processed slides 15: bar 21, sliding rod 18B, every rod block 20 and every heating block 22. Cover 23 is either opened or removed and processed slide cartridge assemblies 11 are removed from tissue processing apparatus 10 by the operator.

Referring now to the structural details of the cartridge assembly 11, FIGS. 5-10 depict various views of cartridge assembly 11 for use with IHC tissue processing system 10 of FIGS. 1-3. Cartridge assembly 11 generally includes a fluid pack 17 that is removably mounted to a cartridge frame 56, and a laboratory slide 15 that is removably mounted to one or both of cartridge frame 56 and fluid pack 17.

Figure 9:
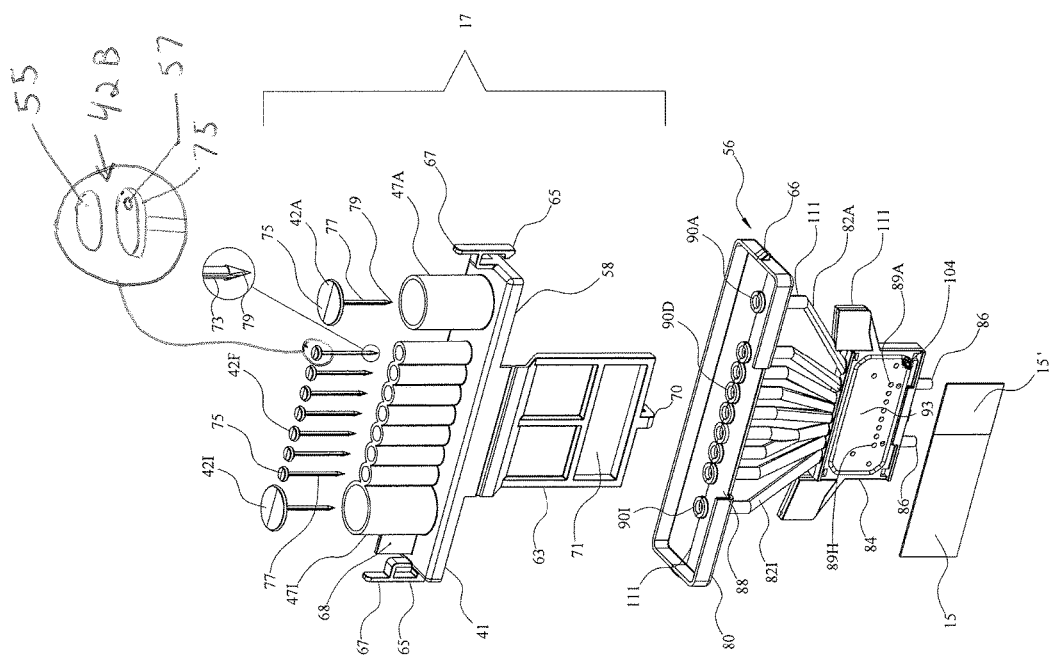
Figure 10:
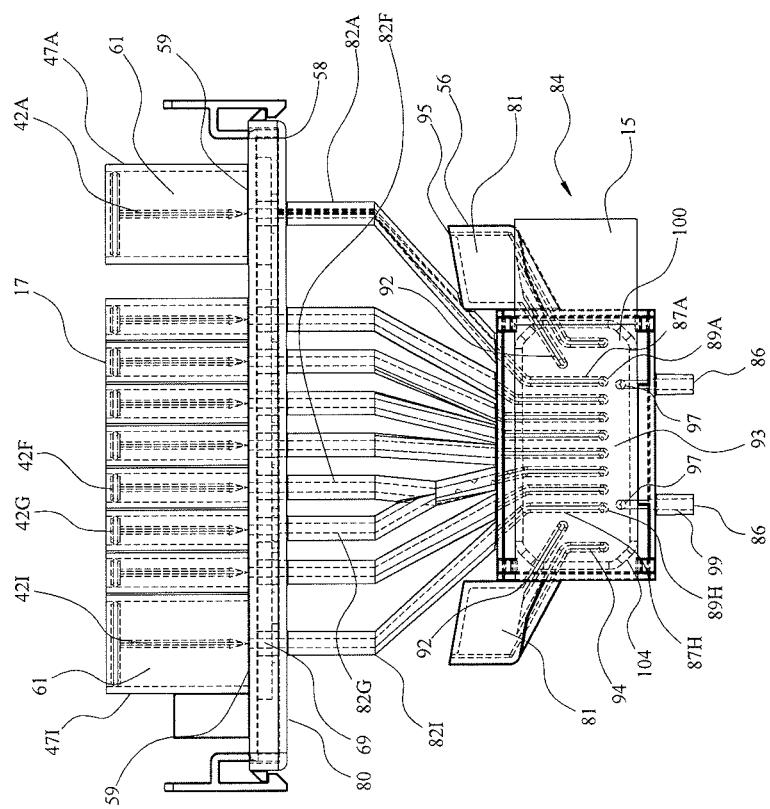
FIG. 10 depicts a phantom rendering of the interior fluid passageways of the cartridge assembly of FIG. 5.

Referring now to fluid pack 17 of cartridge assembly 11, as best shown in FIGS. 5, 9 and 10, fluid pack 17 of cartridge assembly 11 includes a housing 41, which may be composed of plastic, for example, or any other material. Housing 41 generally includes a rectangular base 58, a plurality of fluid-containing wells 47A-47I (referred to as wells 47) extending upwards from rectangular base 58A, and a connector 63 extending downward from one side of rectangular base 58.

Figure 12:
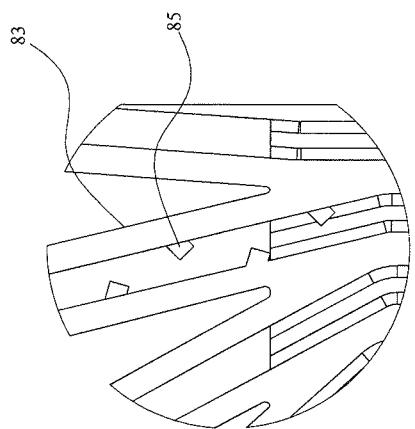
FIG. 12 is a detailed view of the merged fluid passageways of FIG. 11.
Figure 11:
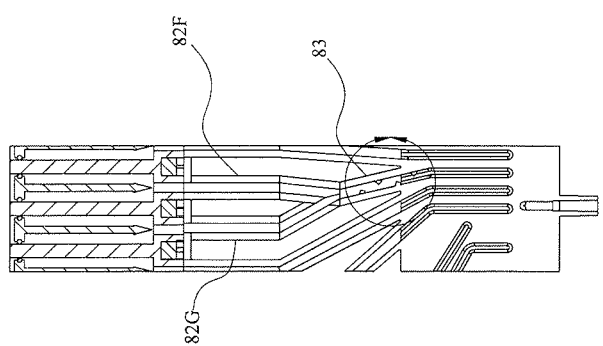
FIG. 11 is a cross-sectional view of the cartridge assembly of FIG. 8 taken along the lines C-C, revealing the merged fluid passageways of the cartridge.

Each fluid-containing well 47 is provided in the form of a hollow cylinder that extends upwardly from rectangular base 58. As shown in FIG. 8, wells 47 are aligned across a lateral axis of base 58. Well 47A is spaced apart from well 47B. Wells have different diameters and lengths for containing different volumes of fluid. For example, wells 47A and 47I have a larger diameter than the other wells 47. Also, wells 47F and 47G have a shorter length than the other wells 47 because their respective pins 42F and 42G are actuated simultaneously, thereby simultaneously delivering two different fluid streams to slide 15, which are later merged into one fluid stream, as shown in FIGS. 10-12. Alternatively, although not shown, wells 47F and 47G may have the same length as the other wells 47

As best shown in FIG. 10, the hollow interior region 61 of each well 47 is filled with a fluid. According to one example of the invention, wells 47A and 47I contain a relatively large volume of buffer solution, whereas the remaining wells 47B-47H contain a reagent solution. The buffer solutions in wells 47A and 47I may differ from each other, and, similarly, the reagent solutions in wells 47B-47H may also differ from each other. The reagent and buffer solutions may be disposed of in different waste reservoirs 50A and 50B, for example.

As best shown in FIGS. 10 and 21, ports 69 extend downward from the bottom side of base 58 beneath each well 47. In an assembled form of cartridge assembly 11, each port 69 of fluid pack 17 is positioned to be aligned with a respective fluid entrance port 90 of cartridge frame 56 to deliver fluid therefrom.

Referring still to FIG. 21, a puncturable or rupturable membrane 59 covers the bottom end of each well 47 to prevent the inadvertent escapement of fluid from well 47. Membrane 59 is a separate sheet of material that is positioned at the bottom end of each well 47. Alternatively, membrane 59 could be a thin piece of plastic integral with base 58 in lieu of using a separate sheet of material.

Figure 15:
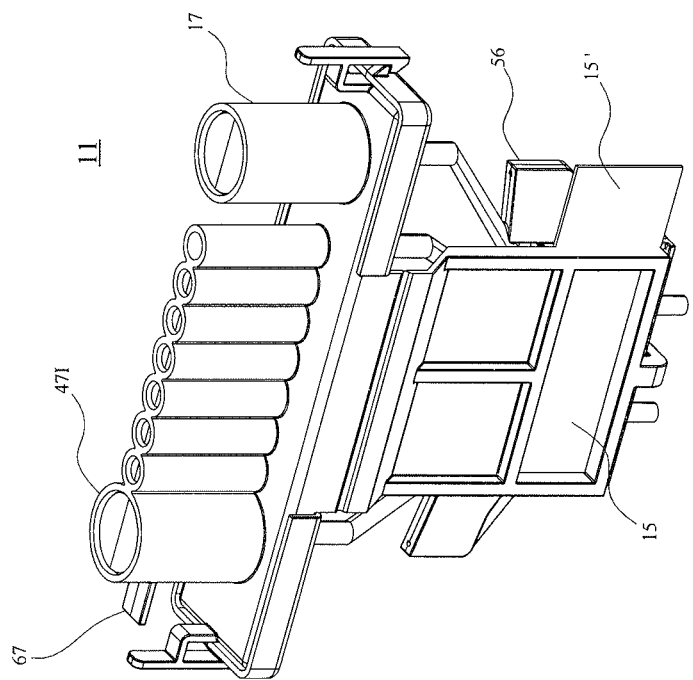
FIG. 15 is a perspective view of another cartridge assembly having a horizontal mounting tab for a bar code.

Referring back to FIG. 9, rectangular base 58 of fluid pack 17 includes a vertically extending tab 68 for accommodating a bar code label (not shown). Alternatively, as shown in FIG. 15, tab 67 for accommodating a bar code label may extend horizontally from a well 47, such as well 47I as shown. Also, a bar code label may also be printed or applied to tab 15' of slide 15. The above-described bar code reader of tissue processing apparatus 10 is configured to read the bar code label attached to tab 68, tab 67 and/or slide tab 15'.

Connector 63 is provided for releasably attaching slide 15 to cartridge frame 56. Connector 63 extends downward from one side of base 58. Connector 63 includes a window opening 71 through which slide 15 can be viewed by an operator. An L-shaped clip 70 is provided at a distal end of connector 63 for releasable attachment to cartridge frame 56. The clip attachment between fluid pack 17 and cartridge frame 56 is best shown in FIG. 14, which is a cross-sectional view of cartridge assembly 11 of FIG. 6 taken along the lines A-A.

Referring now to FIG. 14, clip 70 includes a ramp surface 74 that releasably engages a ramp surface 76 on the bottom end of cartridge frame 56. Ramps 74 and 76 each have angled leading surfaces for sliding over each other upon engaging clip 70 with ramp 76, and angled trailing surfaces for bearing against each other upon seating ramps 74 and 76 to prevent inadvertent removal of clip 70 from cartridge frame 56. Clip 70 also has an outwardly extending tab 78 for releasing clip 70 from ramp 76. In use, tab 78 is flexed downward to separate clip 70 from ramp 76.

Referring back to FIGS. 6 and 9, resilient clips 65 are also positioned on the both short sides of rectangular base 58 for releasably engaging with corresponding ramps 66 (see FIG. 9) that are provided on the short sides of top portion of cartridge frame 56. Resilient clips 65 are provided to releasably secure fluid pack 17 to cartridge frame 56. Clips 65 and ramps 66 each have angled surfaces for sliding over each other upon engaging a clip 65 with a ramp 66, and flat surfaces for bearing against each other upon seating clip 65 on ramp 66 to prevent inadvertent removal of clip 65 from ramp 66. Clips 65 have an upwardly extending tab 67 for releasing clip 65 from ramp 66. In use, tabs 67 are flexed inwardly toward wells 47 to separate clip 65 from ramp 66.

Referring still to FIGS. 6 and 9, slotted pins 42A-42I (referred to either individually or collectively as pin(s) 42) of fluid pack 17 are moveably positioned in the interior of wells 47A-47I, respectively. Pins 42A and 42I are structurally equivalent, and pins 42B through 42H are also structurally equivalent. Each pin 42 includes a large diameter cylindrical portion 75 and a small diameter spike portion 77 extending downward from the underside of cylindrical portion 75. Pins 42 may be composed of plastic or metal, for example. The large diameter cylindrical portion 75 of pins 42A and 42I are larger than large diameter cylindrical portion 75 of pins 42B through 42H.

Large diameter cylindrical portion 75 of pin 42 is configured to seal against the revolved interior wall of a well 47 to prevent the escapement of fluid at the interface between pin 42 and well 47. A seal may be positioned around the large diameter cylindrical portion 75 of pin 42 to seal against the revolved interior wall of a well 47. The overall diameter of cylindrical portion 75 may vary to conform to the different well sizes. The shape of cylindrical portion 75 may also vary so long as it conforms to the shape of the interior of the well in which it is positioned. Cylindrical portion 75 has a flat top surface upon which piston 40 bears.

As shown in the detailed view in FIG. 9, the top end one of pin 42B is shown exploded. The cylindrical portion 75 of pin 42B has a hole 57 defined through its thickness. A sticker 55 is applied to the top surface of cylindrical portion 75 to conceal hole 57. In the course of assembling fluid pack 17, each well 47 is first filled with a fluid by a spike (not shown), for example. Thereafter, the pin 42 is positioned in the fluid-filled well 47, and, as pin 42 is lowered into well 47, the air trapped in well 47 escapes through hole 57. Thereafter, the sticker 55 is applied to the top surface of cylindrical portion 75 to conceal hole 57. Although only one pin 42B is shown exploded in the detailed view in FIG. 9, it should be understood that all of the pins include a similar hole and sticker arrangement.

Slotted spike portion 77 of pin 42 has a sharp tip 79 for puncturing membrane 59. As best seen in the detail view of FIG. 9, spike portion 77 has a slot 73 along its entire length. In use, after sharp tip 79 has punctured membrane 59, the slotted design of spike portion 77 permits the fluid to flow downward along slot 73 of spike 77, past membrane 59 and into cartridge frame 56.

Referring now to cartridge frame 56 of cartridge assembly 11, which is best shown in FIGS. 9 and 10, cartridge frame 56 generally includes a rectangular-shaped base 80 for connecting to fluid pack 17, a series of fluid flow conduits 82 extending downward from base 80, a fluid chamber body 84 positioned below the fluid flow conduits 82, and two drain ports 86 extending below the fluid chamber body 84 though which fluid exits cartridge assembly 11.

Cartridge frame 56 may be formed by an injection molding process and composed of plastic, for example. Although not shown, conduits 82 may be connected together by webs of material if cartridge frame 56 is injection molded. Cartridge frame 56 may be formed from two molded parts that are ultrasonically welded together at intersection lines 111 (see FIGS. 9 and 14).

Referring now to the individual features of cartridge frame 56, rectangular-shaped base 80 of cartridge frame 56 includes ramps 66 defined on its short-length sides for releasably attaching to resilient clips 65 of fluid pack 17, as was described previously. A rectangular-shaped cut-out 88 is defined on one of the long-length sides of base 80 to accommodate connector 63 of fluid pack 17. Those of ordinary skill in the art will recognize that connector 63 of fluid pack 17 could extend further outward from base 80 thereby rendering superfluous cut-out 88. A series of fluid entrance ports 90A-90I (referred to either collectively or individually as port(s) 90) are provided on the top surface of base 80. In an assembled form of cartridge assembly 11, wells 47A-47I are radially aligned with fluid entrance ports 90A-90I, such that fluid in wells 47A-47I can ultimately pass downward through fluid entrance ports 90A-90I, respectively.

A plurality of fluid flow conduits 82A-82I (referred to either collectively or individually as conduit(s) 82) are fluidly connected to fluid entrance ports 90A-90I, respectively, at the bottom end of base 80, such that fluid in fluid entrance ports 90A-90I can ultimately pass downward through conduits 82A-82I, respectively. Each fluid flow conduit 82 includes a hollow region through which fluid can flow either by the force of gravity or by assistance using vacuum pump 54.

Each conduit 82 includes a straight segment at the top and an angled section at the bottom leading to fluid chamber 84. Alternatively, the entire length of conduit 82 may be straight. As best shown in FIG. 21, the straight segment of each conduit 82 is long enough to accommodate the length of a depressed pin 42 (such as pin 42B) such that the sharp tip of pin 42 cannot pierce the sidewall of conduit 82.

FIGS. 10-12 depict conduits 82F and 82G merging into a single conduit 83. Conduit 83 includes mixers 85, in the form of protrusions positioned along the length of conduit 83 and extending radially into the fluid passageway of conduit 83. Mixers 85 are configured to mix the fluid streams arriving from conduits 82F and 82G.

As best shown in FIG. 10, fluid chamber body 84 of cartridge frame 56 is connected to the bottom end of conduits 82. Fluid chamber body 84 includes a rectangular body defining a slide receiving area for receiving slide 15 and having a network of internally formed fluid passageways for transporting fluid therethrough.

Figure 13:
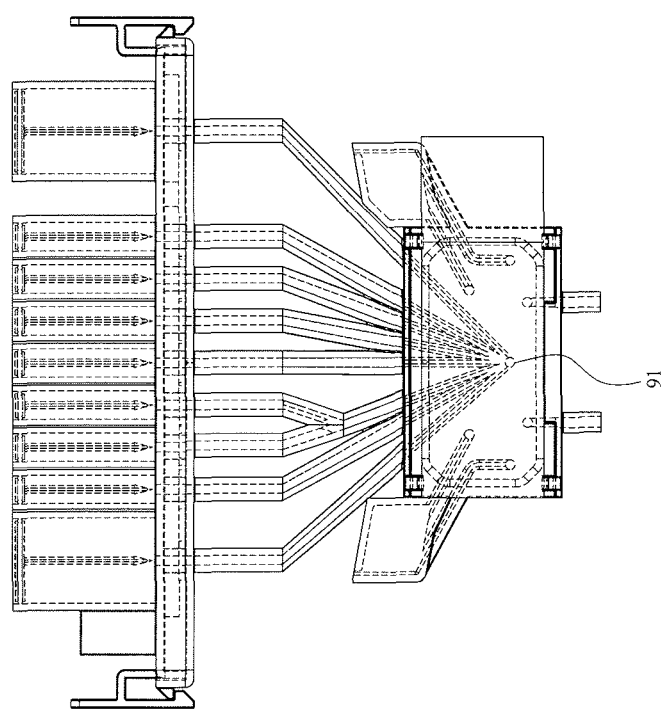
FIG. 13 depicts a phantom rendering of a different cartridge, similar to that of FIG. 5, revealing alternative interior fluid passageways.

More particularly, a plurality of internally formed fluid passageways 87A-87H (referred to either collectively or individually as fluid passageway(s) 87) formed in body 84 are fluidly connected to the bottom end of conduits 82A-82E, 83, 82H and 82I, respectively, for receiving fluid therefrom. Fluid passageways 87A-87H terminate at exit ports 89A-89H, respectively, that are defined on the planar surface 93 (see FIG. 10) of fluid chamber body 84 that faces the slide 15. Alternatively, as shown in FIG. 13, fluid passageways 87A-87H can terminate at a single common exit port 91 in lieu of separate exit ports 89 shown in FIG. 10. In operation, fluid travels from conduits 82, through passageways 87 and is distributed through exit ports 89.

A reaction chamber 100 is defined between planar surface 93 of body 84 and the surface of slide 15 that faces planar surface 93. A gasket 104 sandwiched between slide 15 and planar surface 93 circumscribes the rectangular outer boundaries of reaction chamber 100. Gasket 104 may be mounted and affixed in a channel that is formed on planar surface 93. In operation, once fluid travels through exit ports 89 (or exit port 91 of FIG. 13) of body 84, the fluid is distributed into reaction chamber 100 for reacting with the tissue sample (for example) that is affixed to slide 15.

As best shown in FIGS. 10 and 21, two condensation chambers 81 each defining a hollow interior region are positioned on opposite sides of body 84. Chambers 81 are positioned at an elevation substantially above slide 15. The hollow interior region of each condensation chamber 81 is fluidly connected to reaction chamber 100 by an entrance passageway 92 and an exit passageway 94. Passageways 92 and 94, like passageways 87, are internally formed in body 84.

In operation, some of the reagents are processed at high temperatures, e.g., 98 degrees Celsius. The high temperatures promote faster evaporation of the reagent fluid in the reaction chamber that may result in an insufficient amount of reagent in the reaction chamber. To prevent this occurrence, condensation chambers 81 are each designed to collect the vapors emanating from reaction chamber 100 through entrance passageway 92, cool those vapors to liquid form, and eventually return the cooled liquid reagent into reaction chamber 100 via exit passageways 94. The lower surface of each chamber 81 is slanted so that the condensed vapor returns to the reaction chamber 100 by gravity. The entrance port of passageway 92 in reaction chamber 100 is positioned at a higher elevation than exit ports 89 and the exit port of passageway 94 in reaction chamber 100. Although passageway 92 is primarily an entrance passageway and passageway 94 is primarily an exit passageway, it should be understood that fluid can enter and exit through either passageway 92 or 94.

An atmospheric port 95 is provided at the top end of each condensation chamber 81. In operation, pump 54 (see FIG. 4) is configured to draw a stream of air through atmospheric port 95 and into fluid reaction chamber 100 (via passageways 92 and 94) in order to drain the fluid within reaction chamber 100 without inadvertently drawing depressed pins 42 further downward toward reaction chamber 100 due to the vacuum pressure. The air stream can also be used to actively cool slide 15 via the forced convection of air.

Two drain holes 97 are provided on planar surface 93 at an elevation below holes 89 and passageways 92 and 94 to drain fluid from reaction chamber 100. Drain passageways 99, which are formed internally in body 84, connect drain holes 97 to independent drain ports 86.

In operation, when cartridge assembly 11 is connected to a cartridge receiving block 28, as shown in FIG. 1, and depending upon the open/closed setting of solenoid valves 46, fluid exits reaction chamber 100 through one of the drain holes 97 either under the force of gravity or vacuum pressure produced by pump 54. The fluid then passes through one of the drain passageways 99, then through one of the drain ports 86 of cartridge assembly 11, then through one of the fluid drain ports 29 of cartridge receiving block 28, and then into the network of conduits 44 and 48 shown in FIG. 4 and into one of waste reservoirs 50A or 50B (see fluid direction arrows in FIG. 4). The particular pathway of the fluid is dictated by the open/closed setting of solenoid valves 46, as was described with reference to FIG. 4.

Figure 17:
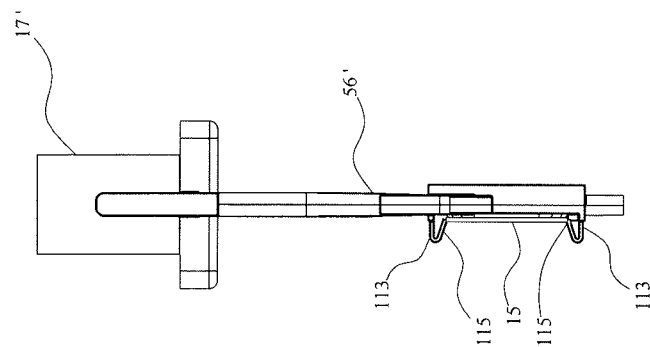
FIG. 17 is a right side elevation view of the cartridge assembly of FIG. 16.
Figure 16:
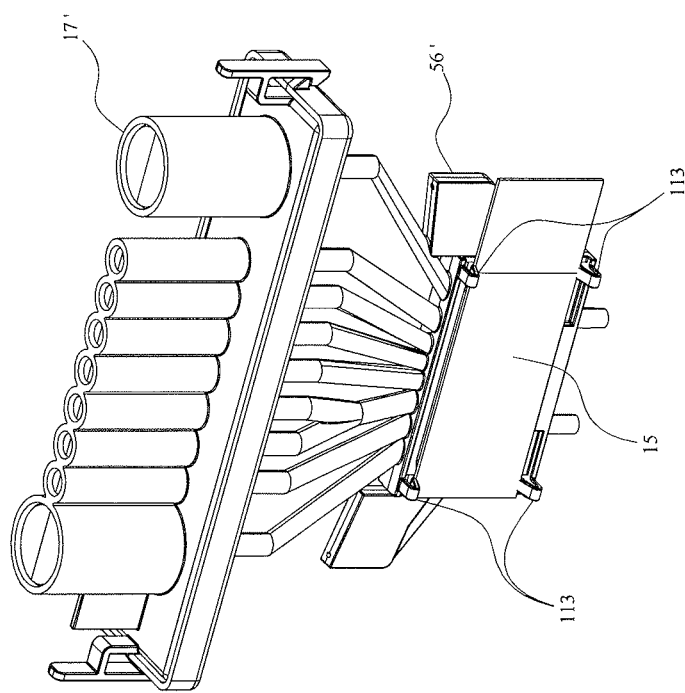
FIG. 16 is a perspective view of another cartridge assembly having an alternative means for attaching a laboratory slide to the cartridge frame.

FIGS. 16 and 17 depict a different attachment arrangement for slide 15. In lieu of connector 63 of fluid pack 17 shown in FIG. 6, a different connector comprising a series of four flexible barbs 113 extend from planar surface 93 (see FIG. 9) of cartridge frame 56' to releasably mount slide 15 to cartridge frame 56'. Each flexible barb 113 includes a recessed area at its proximal base end (i.e., closest to surface 93) that is sized to retain the thickness dimension of slide 15, and a flexible distal end that is capable of flexing away from slide 15 in order to release slide 15 from cartridge frame 56'. The leading surface 115 of each barb 113 is angled to guide the attachment of slide 15 onto cartridge frame 56'.

Figure 18:
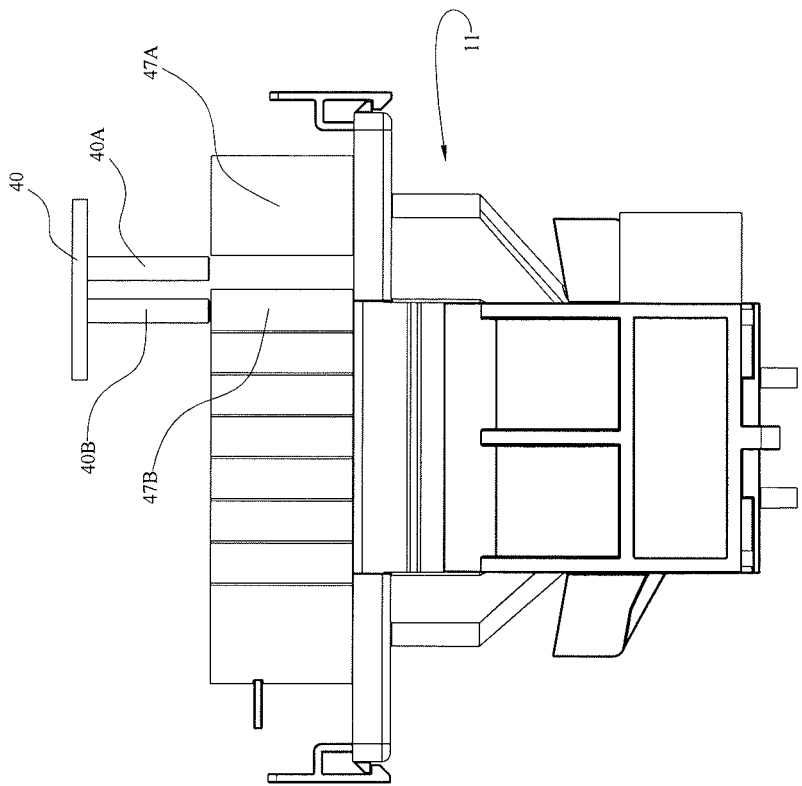
FIG. 18 is a perspective view of the cartridge assembly of FIG. 5, and pistons of the IHC tissue processing system shown depressing a pin in one of the cylinders of the cartridge.

FIGS. 18-22 depict piston 40 interacting with different pins 42 of cartridge assembly 11. Piston 40 includes a flat plate 40C, which is moved along the X, Y and/or Z axes by moveable carriage 36 (see FIG. 1), and two cylindrically-shaped solid rods 40A and 40B extending downward from flat plate 40C. Piston 40 is operable to selectively depress pins 42 of cartridge assemblies 11 to deliver fluid stored within wells 47 through cartridge assemblies 11, as described above. As best shown in FIG. 18, both rods 40A and 40B are used to move a pin 42 in the large wells 47A and 47I, whereas, as shown in FIGS. 19-22, only one of the rods 40A and 40B is used to move a pin 42 in the small wells 47B-47H.

Figure 19:
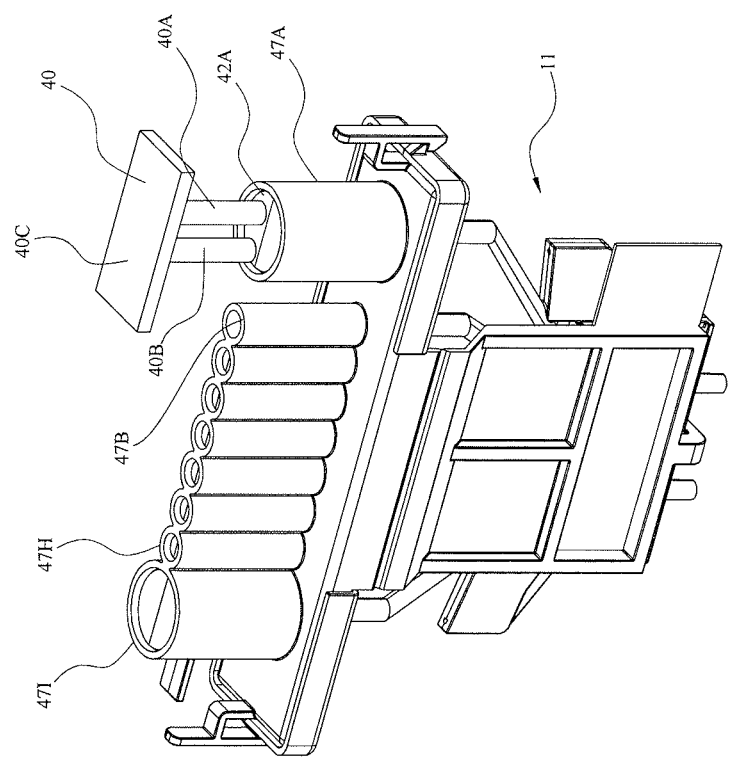
FIG. 19 is a front elevation view of the cartridge assembly of FIG. 18 with the pistons of the IHC tissue processing system shown pushing a different pin of the cartridge.

In FIG. 18, rods 40A and 40B are positioned to depress pin 42 in large well 47A. In FIG. 19, rod 40A is positioned to travel in the empty space between wells 47A and 47B, whereas rod 40B is positioned to depress pin 42 in well 47B. In FIGS. 20 and 21, pin 42B is already depressed, rod 40A is positioned to freely travel in well 47B without depressing pin 42B, and rod 40B is positioned to depress pin 42C in well 47C. In FIG. 22, rods 40A and 40B are positioned to simultaneously depress pins 42F and 42G in wells 47F and 47G, respectively. As shown in FIGS. 11, 12 and 22, upon depressing pins 42F and 42G in wells 47F and 47G, fluid travels from those wells into conduits 82F and 82G, respectively, and then into merged conduit 83. Mixers 85 in merged conduit 83 mix the fluid streams emanating from conduits 82F and 82G before the combined fluid stream is delivered into reaction chamber 100 of cartridge assembly 11.

Figure 23:
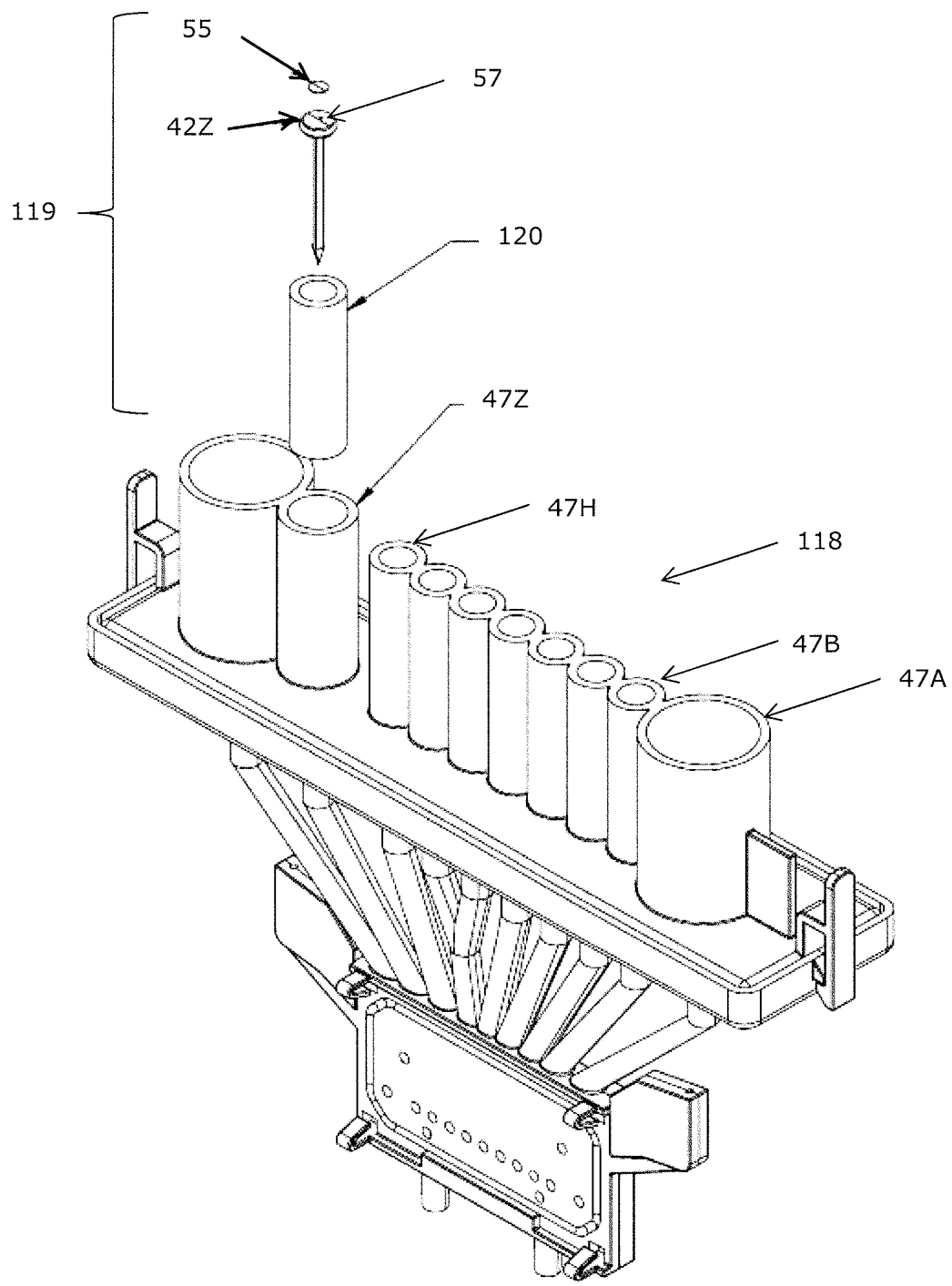
FIG. 23 is a perspective view of a kit comprising a different cartridge assembly and a reagent module assembly.

FIG. 23 depicts a perspective view of a kit comprising another cartridge assembly 118 and a reagent module assembly 119 for use with the cartridge assembly 118. Cartridge assembly 118 is substantially similar to cartridge assembly 11 and only the differences between those cartridge assemblies will be described hereinafter. Cartridge assembly 118 includes an empty well 47Z that is sized to accommodate well 120 of reagent module assembly 119. The bottom end of empty well 47Z is sealed. Empty well 47Z has a diameter that is larger than the small-diameter wells 47B-47H, yet smaller than the large-diameter well 47A.

Reagent module assembly 119 is a sub-assembly that includes well 120, pin 42Z and sticker 55. Well 120 is a closed-end cylinder defining an interior for holding a fluid. The outer and inner diameter of well 120 matches that of the small-diameter wells 47B-47H. Pin 42Z includes an aperture 57, and is substantially the same as the other small-diameter pins 42B-42H that were described previously.

In use, cartridge assembly 118 is supplied to a third party reagent pack supplier or end-user, and the third party supplier or end-user first fills the empty well 120 with fluid using a syringe (for example). Pin 42Z is then inserted into the fluid-filled well 120, while air in well 120 is permitted to escape through aperture 57. Sticker 55 is then applied to the top end of pin 42Z to seal aperture 57. The now-assembled reagent module assembly 119 is inserted into the empty well 47Z of cartridge assembly 118.

Pin 42Z is operated in the same manner as the other pins 42, i.e., to deliver fluid to the reaction chamber of cartridge assembly 118, with the exception that pin 42Z may be operated to first pierce the bottom end of well 120 and then pierce the seal of well 47Z.

Figure 24:
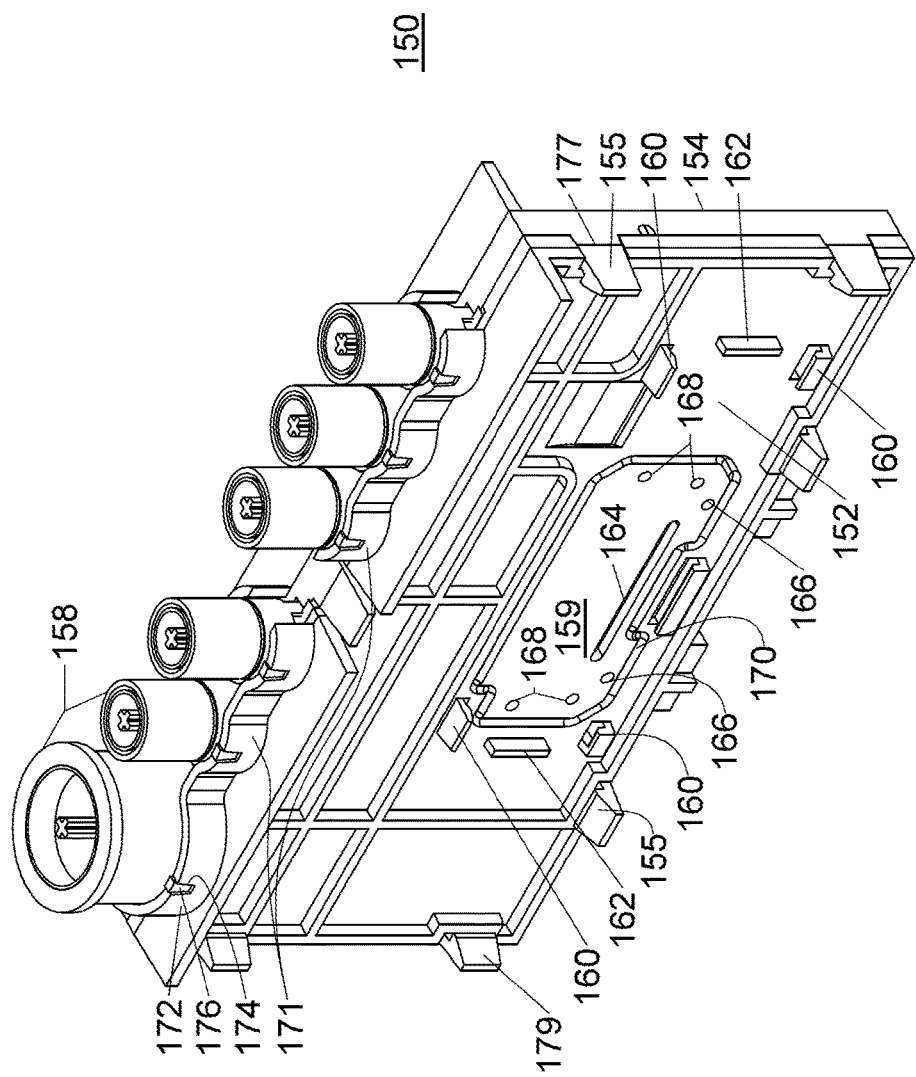
FIG. 24 is a perspective view of another cartridge assembly shown assembled.

FIGS. 24 and 25 depict an alternative cartridge assembly 150. The cartridge assembly 150 is similar to the cartridge assembly 11, and only the primary structural differences between those cartridge assemblies will be described hereinafter. Cartridge assembly 150 includes a slide support frame 152, a fluid delivery frame 154 that is connected to the frame 152 by clips 155 (6 shown), a seal 156 sandwiched between the frames 152 and 154, and a plurality of wells 158 (six shown) that are mounted atop the frames 152 and 154.

Referring now to the individual components of cartridge assembly 150, the outward facing surface of slide support frame 152 includes clips 160 and stops 162 for releasably captivating a laboratory slide (not shown). As best shown in FIG. 26, an exit port 164 in the form of an elongated slot (analogous to the combined exit ports 89), drain holes 166 (like drain holes 97) and condensation chamber openings 168 (like the openings to passageways 92 and 94) are formed through the thickness of the slide support frame 152.

A gasket 170 (like gasket 104) is mounted to the outward facing surface of the slide support frame 152, and, in use, is sandwiched between the frame 152 and the laboratory slide (not shown) that is mounted to the frame 152. The gasket 170 defines the perimeter boundaries of a reaction chamber 159. The gasket 170 may be a separate component that is seated in a groove (groove optional) formed in the outward facing surface of the slide support frame 152. The gasket 170 may be glued or liquid injected using a cured silicone, for example, or other type of rubberized material. Alternatively, the gasket 170 may be overmolded directly on the frame 152, and, thus, integral with the frame 152.

Two walls 171 extend from the top surface of the frame 152 and each wall includes a series of semi-circular surfaces 172 for accommodating a portion of the wells 158. A small trapezoidal-shaped cutout 174 is provided at the top edge of each semi-circular surface 172 for frictionally engaging with a mating trapezoidal-shaped protrusion 176 that is disposed on the side surface of each well 158. A series of rectangular cutouts 177 are provided on the perimeter of the frame 152 for engaging with mating clips 155 of the fluid delivery frame 154.

The fluid delivery frame 154 includes a series of clips 155 at its perimeter for mating with the cutouts 177 on the frame 152, as previously described. Each clip 155 includes an angled free end 179. Upon assembling the frames 152 and 154 together, each clip 155 flexes outwardly as the angled surface 179 passes along the cutout 177. Once the angled surface 179 passes through its respective cutout 177, the clip 155 snaps inwardly, thereby securing the clip 155 (and its frame 154) to the frame 152. The frames 152 and 154 can be disconnected by flexing two or more clips 155 outwardly and simultaneously pulling apart the frames 152 and 154.

The fluid delivery frame 154 includes a network of internally formed fluid flow passages through which (i) fluid is transported from respective wells 158 to the reaction chamber 159 of the frame 152 via openings in the seal 156 and the frame 152, (ii) condensation is processed, and (iii) waste fluid is drained. More particularly, a series of fluid entrance ports 184 are provided on the top surface of the frame 154.

A plurality of fluid flow conduits 180A-180F (referred to either collectively or individually as conduit(s) 180) are formed on the interior facing surface of frame 154. Each fluid flow conduit 180 is fluidly connected to a respective fluid entrance port 184 such that fluid that enters a fluid entrance port 184 from a well 158 can ultimately pass downward through the conduit 180, respectively. Two adjacent conduits 180C and 180D combine together into one conduit, like conduits 82F and 82G. The combined passageway may include mixers, like mixers 85. The interior facing side of each conduit 180 is open and covered by the seal 156 to prevent the fluid in one conduit 180 from inadvertently passing into another conduit 180. Fluid passageways 87A-87H terminate at respective exit ports 186.

Two condensation chambers 188 each defining a hollow interior region are positioned on opposite ends of the interior facing side of frame 154. Chambers 188 are positioned at an elevation substantially above the exit ports 186. The hollow interior region of each condensation chamber 188 is fluidly connected to reaction chamber 159 by an entrance passageway 192 and an exit passageway 194 that is positioned beneath the entrance passageway 192. An atmospheric port 196 is provided at the top end of each condensation chamber 188 for exposing the chambers 188 to atmospheric pressure.

In operation, condensation passes through holes 168 of frame 152, then passes through holes 191 of seal 156, then travels along passageways 192 and/or 194 of frame 154 and into or out of each condensation chamber 188.

Two drain ports 195 extend below the exit ports 186 though which fluid exits cartridge assembly 150. In operation, waste fluid collected within reaction chamber 159 ultimately exits through drain holes 166 of frame 152, then passes through holes 193 of seal 156, and then travels through drain ports 195.

Two walls 189 extend upward from the top surface of the frame 154 and each wall 189 includes a series of semi-circular surfaces (like surfaces 172) for accommodating the base portion of the wells 158. Each semi-circular surface of the walls 189 is positioned directly opposite a semi-circular surface 172 of the wall 171 of the frame 152. In an assembled form of the cartridge 150, the wells 158 are sandwiched between opposing semi-circular surfaces 171 and 172 of the frames 152 and 154, respectively.

The plurality of fluid-containing wells 158 are mounted atop the frames 152 and 154, as noted above. Two of the wells 158 are shown exploded in FIG. 25. Each well 158 includes a hollow cylinder 200 for containing fluid (such as a buffer solution or a reagent solution), and a pin 202 that is movably positioned within the hollow cylinder 200 for delivering the fluid into the cartridge 150.

Each cylinder 200 of a well 158 includes two clips 206 on its lower end for attaching to a semi-circular opening formed between the top walls of the frames 152 and 154 at the top end of the cartridge assembly 150. A trapezoidal-shaped protrusion 176 is disposed on the side surface of each well 158 for frictionally engaging with a mating trapezoidal-shaped cutout 174 provided at the top edge of each semi-circular surface 172 of the frame 152.

Each pin 202 includes a slotted spike 204 having a non-circular cross-section. The slotted spike 204 includes a sharp tip on its lower end for puncturing a membrane (not shown) at the base of the cylinder 200, and a bearing surface 205 on its upper end that is to be contacted by a piston (such as piston 40) during operation for moving the pin 202 in a downward direction. The slotted spike 204 is fixed to a cup-shaped member 207. Fluid is contained within the well 158 beneath the cup shaped member 207.

An O-ring gasket 206 is sandwiched between the top surface of the frame 154 (i.e., at fluid entrance port 184) and the bottom end of the cylinder 200 for channeling the fluid distributed from the cylinder into the fluid entrance port 184. The gasket 206 may or may not be considered as constituting part of well 158.

FIG. 25A depicts an alternative well 158', in which the well cylinder 200' includes a step or shoulder 201 defined along its revolved interior surface. In the process of assembling the well 158', the cylinder 200' is first filled with fluid, and the pin 202 is inserted into the cylinder 200'. As the pin 202 is inserted into the cylinder 200', any air that is trapped within the cylinder 200' can escape past the shoulder 201 until the pin 202 snuggly fitted within the small interior diameter of the cylinder 200'.

FIGS. 27 and 28 depict perspective and cross-sectional views of an IHC tissue processing system 222 for processing a laboratory slide 223. Although one station of the IHC tissue processing system 222 for processing a single slide 223 is shown in the figures, it should be understood that the IHC tissue processing system 222 may include any number of stations for processing any number of slides 223. Also, the IHC tissue processing system 222 shares many on the same features as the previously-described tissue processing system 10, and the primary differences between those systems will be described hereinafter.

The IHC tissue processing system 222 generally includes a linear actuator 225 that interacts with a piston carriage 232 to selectively expel fluid from a fluid cartridge assembly 224 onto the slide 223.

The linear actuator 225 includes a reciprocating shaft 226 and a ratchet driver 227 that is fixedly mounted to the end of the reciprocating shaft 226. The ratchet driver 227 is substantially cylindrical and includes a series of ratchet teeth 228 in the form of right-angled ramps that encircle the perimeter of its free end. Each ratchet tooth 228 includes a flat vertical surface 233 and an angled surface 230 that intersects the flat vertical surface 233 at an acute angle. It should be understood that neither the reciprocating shaft 226 nor the ratchet driver 227 are capable of rotation, i.e., those components only translate in a vertical direction.

Although not shown, the motor of the linear actuator 225 may be fixedly mounted to a housing of the IHC tissue processing system 222. Alternatively, the linear actuator 225 may be mounted to a drive device that is capable of moving the linear actuator 225 in the X, Y and/or Z directions for interacting with a plurality of fluid cartridge assemblies 224.

The piston carriage 232 includes a hollow cylinder 234 having an open top end, which is enclosed by a cover 235. The cover 235 may be fixedly mounted to the top open end of the cylinder 234. The bottom end of the hollow cylinder 234 includes a series of holes 236 that are uniformly oriented along an imaginary circle having a central axis that is coincident with the longitudinal axis 'A.' The size, shape, number and location of the holes 236 may vary. A hollow cylindrical protrusion 238 extends upwardly from the bottom end of the hollow cylinder 234. A compression spring 240 is positioned within the interior of the hollow cylindrical protrusion 238.

A sliding member 242 having a cylindrical solid top end and a cylindrical hollow bottom end is positioned above the spring 240. The spring 240 is at least partially positioned within the cylindrical hollow bottom end of the sliding member 242 such that the spring 240 is sandwiched between the sliding member 242 and the bottom end of the hollow cylinder 234. The spring 240 is configured to bias the sliding member 242 in an upward vertical direction away from the bottom end of the cylinder 234. The top end of the sliding member 242 is mounted within a blind hole that is formed on the bottom end of a piston driver 250.

The piston driver 250 includes a horizontal wall 251, which defines the blind hole in which the sliding member 242 is positioned. The wall 251 is positioned within the cylinder 234 at a location below the cover 235. The wall 251 is detached from the cover 235 and is configured to translate in a vertical direction with respect to the cover 235. A ratchet driver 252 extends upward from the horizontal wall 251 and is positioned through a central hole in the cover 235 to an elevation above the cover 235. Like the ratchet driver 227, the ratchet driver 252 is substantially cylindrical and includes ratchet teeth 257 in the form of right-angled ramps that encircle the perimeter of its free end. As best shown in the partial assembly view of FIG. 29B, each ratchet tooth 257 includes a flat vertical surface 253 and an angled surface 255 that intersects the flat vertical surface 253 at an acute angle. The teeth 228 of the ratchet driver 227 are configured to engage and mesh with the teeth 257 of the ratchet driver 252.

The piston driver 250 further includes two cylindrically-shaped pistons 260 that extend in a downward vertical from the lower face of the wall 251. Each piston 260 is configured to interact with a single pin 262 in a fluid-containing well 264 of the fluid cartridge assembly 224 to deliver the fluid to the slide 223. The pistons 260 are arranged about an imaginary circle having a center that is co-aligned with the longitudinal axis 'A,' and the pistons 260 along that imaginary circle.

Figure 29A:
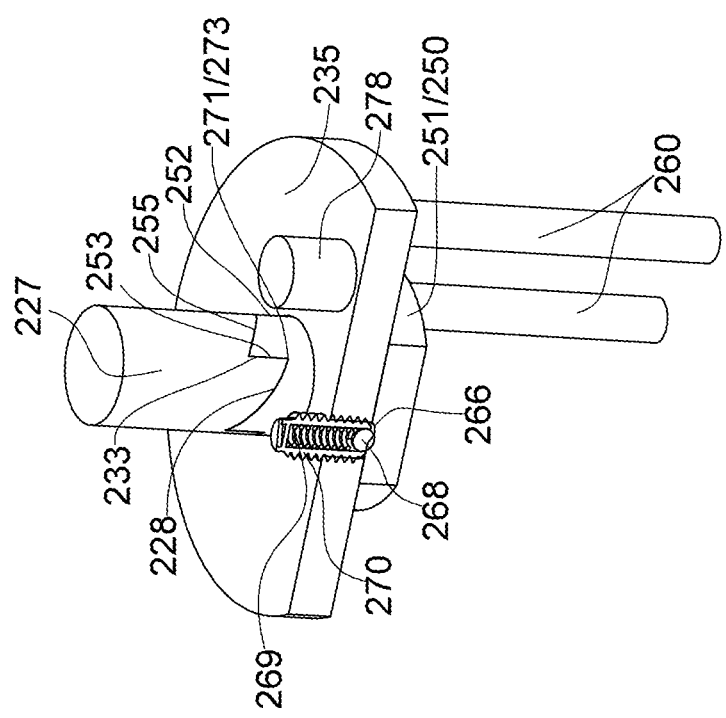
FIGS. 29A and 29B are partial-assembly views of the IHC tissue processing system of FIG. 27 depicting auto-rotation of the piston driver for re-alignment purposes.
Figure 29B:
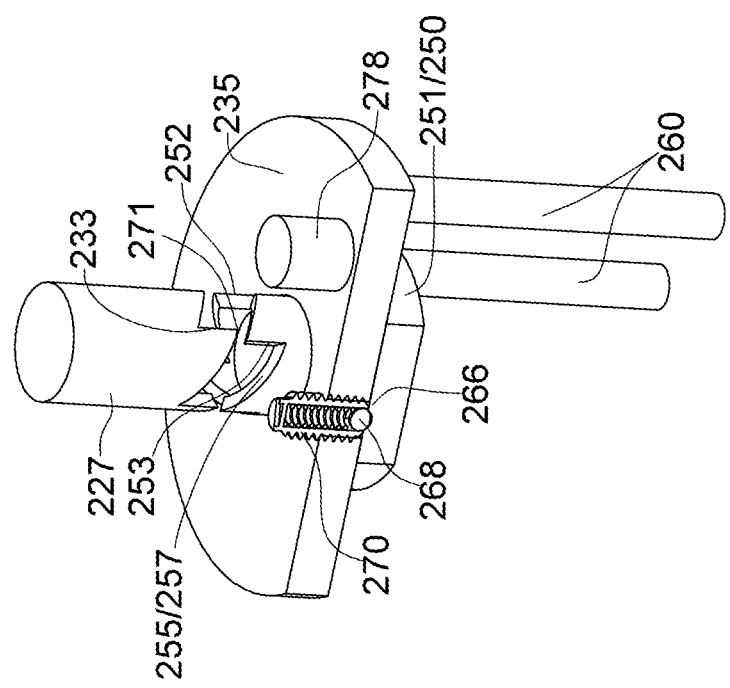
Figure 30:
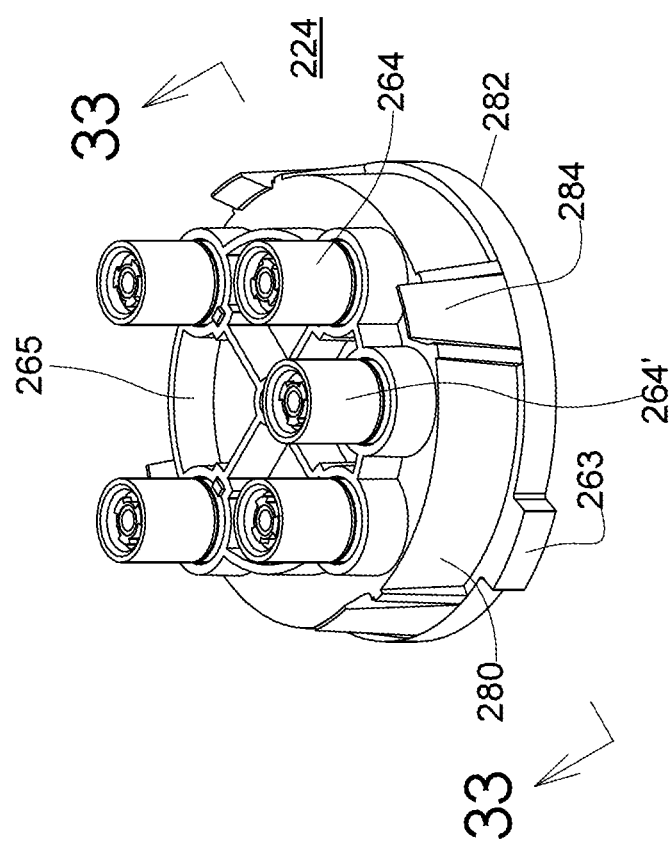
FIG. 30 depicts a top-side perspective view of a cartridge assembly for use with the IHC tissue processing system of FIG. 27.

FIGS. 29A and 29B depicts partial assembly views of the tissue processing apparatus 222 including the piston carriage 232, the cover 235 and the ratchet driver 227 of the linear actuator 225. The cover 235 is shown partially cut-away to reveal the engagement between a ball 268 and a depression 266 formed on the top side of the wall 251. As shown in those views, the top surface of the wall 251 includes a plurality of depressions 266 (one of four shown) that are circumferentially aligned and uniformly spaced apart about the longitudinal axis 'A.' The number of depressions 266 corresponds to the number of radial positions of the piston driver 250. According to this exemplary embodiment, the piston driver 250 has four different radial positions.

A spring-loaded ball 268, which is biased in the downward vertical direction by a spring 269, is movably positioned within a threaded sleeve 270 having a closed top end and an open bottom end. The threaded sleeve 270 is fixed to the cover 235, and the spring loaded ball 268 protrudes from the lower face of the cover 235. The ball 268 is captivated within the sleeve 270.

The force of the springs 269 and 240 causes the ball 268 to center itself in the depression 266, thereby causing the piston driver 250 along with the ratchet driver 252 to rotate by a slight degree. More particularly, after each successive movement of the ratchet driver 227, the interaction between the spring-loaded ball 268 and the depression 266 causes the ratchet driver 252 to rotate to a rotational position where the tooth tips 271 of the ratchet driver 227 are radially aligned with respective angled surfaces 255 of the ratchet driver 252. The purpose of the ball 268 and the depressions 266 are to rotationally advance the ratchet driver 252 of the piston driver 250 immediately following every reciprocating motion (namely, down and up translation) of the linear actuator 225 so that the driver 227 can continuously engage and advance the ratchet driver 252 (along with the entire piston driver 250). The operation of the ball 268 and the depressions 266 will be described in greater detail with reference to the operation of the IHC tissue processing system 222.

Alternatively, as will be described with reference to FIGS. 43A and 43B, the ball 268 and the depressions 266 may be replaced with a set of meshing ramped surfaces (like the teeth of the drivers 227 and 252) on the upper face of the wall 251 and the lower face of the cover 235, which would cause slight auto-rotation of the ratchet driver 252 by virtue of the force of spring 240 following every reciprocating motion of the linear actuator 225.

It should be understood that in the absence of the ball 268 and the depressions 266 or the set of meshing ramped surfaces described above (or other similar auto-rotation feature), the tooth tips 271 of the ratchet driver 227 would continuously engage the same interior corners 273 of the ratchet driver 252, which would prevent the ratchet driver 252 from being rotated as the ratchet driver 227 is translated.

A sensor 278 is mounted to the cover 235 for sensing a rotational position of the piston driver 250. The sensor 278 is either directly or indirectly connected to a control unit (not shown) for communicating the position of the piston driver 250 to the central unit. Based upon the information received from the sensor 278, the control unit can determine the rotational position of the piston driver 250, which fluid containing wells 264 have been emptied by the pistons 260, and/or which fluid containing well 264 will be emptied next by the pistons 260. The sensor 278 may be a Hall effect sensor, for example, that communicates with a magnet (not shown) that is mounted to the top surface of the wall 251 of the piston driver 250. Those skilled in the art will recognize that the numerous other devices and methods for sensing a rotational and/or translation position of an object exist.

FIGS. 30-33 depict the fluid cartridge assembly 224 of the tissue processing apparatus 222. Fluid cartridge assembly 224 includes a well support frame 280, a fluid delivery frame 282 that is connected to the frame 280 by clips 284 (five shown), a seal 286 sandwiched between the frames 280 and 282, and a plurality of wells 264 that are mounted atop the frame 280.

Referring now to the individual components of cartridge assembly 224, the well support frame 280 is a substantially cylindrical body including internal fluid flow passages through which fluid is distributed from the wells 264. A series of openings 288 are formed by cylindrical walls extending from the top surface of the frame 280 in which individual wells 264 are mounted. The cylindrical walls are interconnected by ribs extending from the top surface of the frame 280. The wells 264 may be removably mounted to the cylindrical walls. Each opening 288 includes a slot 290 for frictionally engaging with a mating protrusion 291 that is disposed on the side surface of a mating well 264. A series of slots 292 are provided on the perimeter of the frame 280 for engaging with mating clips 284 of the fluid delivery frame 282.

The fluid delivery frame 282 is also a substantially cylindrical body including internal fluid flow passages through which fluid is distributed from the wells 264. The fluid delivery frame 282 includes clips 284 at its perimeter for mating with the slots 292 on the frame 280, as previously described. An alignment tab 263 extends from the outer surface of the frame 282, and the tab 263 may be used for rotationally aligning the fluid cartridge assembly 224 into a housing (not shown and optional) in which it is mounted. Although not shown, the fluid delivery frame 282 may have a funnel-like conical shape to facilitate the draining of fluid by gravity.

The fluid cartridge assembly 224 includes five wells 264. The structure of each well 264 is substantially identical to the wells 158 of FIG. 25. The wells 264 are oriented along an imaginary circle having a center axis that is co-aligned with the longitudinal axis 'A.' Four of the wells 264 are evenly spaced apart along the circle by 90 degrees. One of the wells 264', however, is positioned between two of the wells 264 that are spaced apart by 90 degrees. In other words, the well 264' is separated from each of its adjacent wells 264 by 45 degrees about the imaginary circle. The well 264' is positioned in that location such that when one of the pistons 260 is positioned within well 264', the other of the two pistons is also positioned within a well 264 that is directly adjacent to well 264'.

The arrangement of the pistons 260 and the wells 264 and 264' makes it possible to simultaneously deliver fluid from two of the wells 264 and 264' into the internal fluid passageways of the fluid cartridge assembly 224 and onto the slide 223. When no piston 260 is positioned within well 264', then one piston 260 of the two pistons 260 is positioned inside of a well 264 and the other piston 260 of the two pistons 260 is positioned in one of the gaps 265 defined between two adjacent wells 264.

Figure 31:
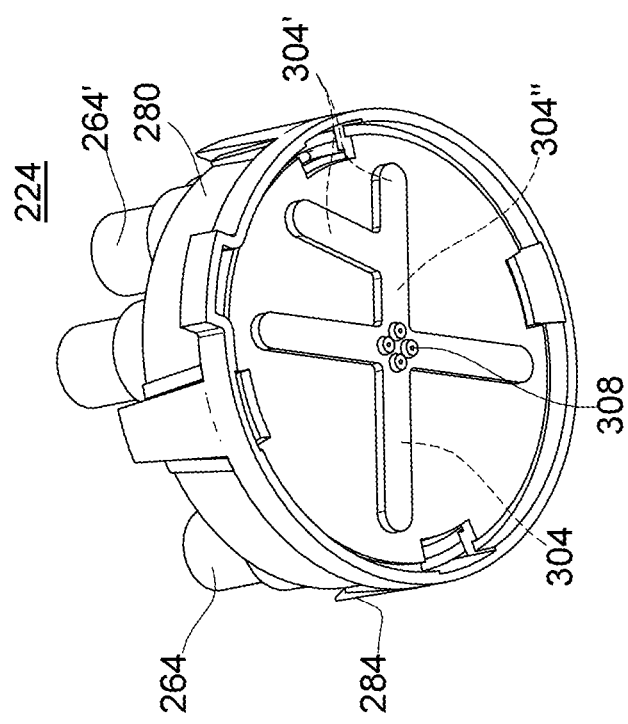
FIG. 31 depicts a bottom-side perspective view of the cartridge assembly of FIG. 30.
Figure 32:
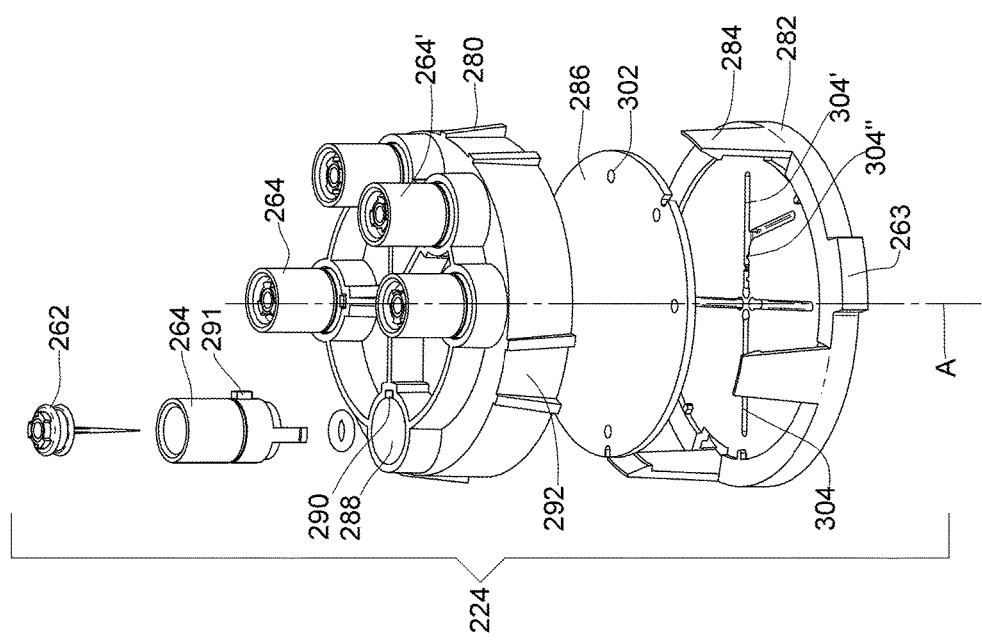
FIG. 32 depicts an exploded view of the cartridge assembly of FIG. 30.
Figure 33:
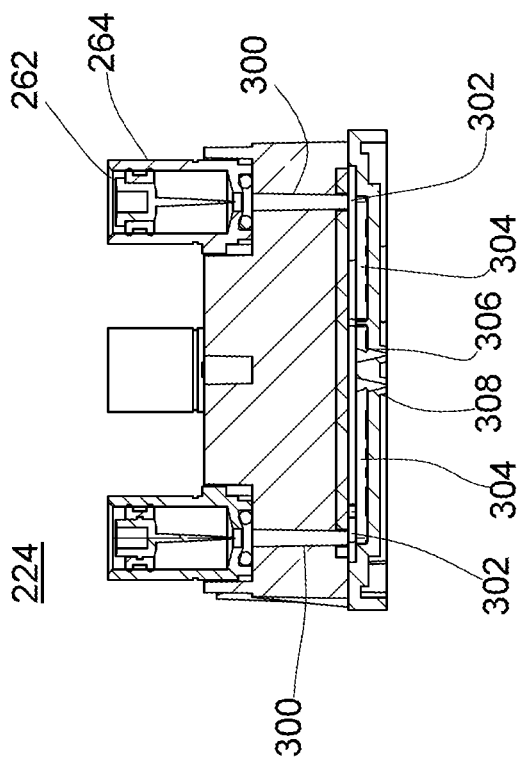
FIG. 33 depicts a cross-sectional view of the cartridge assembly of FIG. 30 taken along the lines 33-33.

FIGS. 31-33 depict the fluid flow passages of the fluid cartridge assembly 224. The internal fluid flow passages extending beneath the wells 264 each includes a vertical passage 300 formed in the frame 280 that extends beneath each well 264. The vertical passage 300 connects to a hole 302 in the seal 286, which connects to an elongated slot 304 that is formed on the top surface of the frame 282. The end of each elongated slot 304 terminates at a frusto-conical shaped exit port 306, through which the fluid exits the fluid cartridge assembly 224 and is directed onto the slide 223.

Two adjacent elongated slots 304' are interconnected and combine together into one elongated slot 304". The combined elongated slot 304" include mixers, like mixers 85, for mixing the fluid streams travelling through the slot 304". The adjacent elongated slots 304' correspond to the well 264' and a well 264 that is directly adjacent to well 264', such that fluid is delivered from the wells 264' and 264 into the elongated slots 304'.

As best shown in FIG. 31, each frusto-conical shaped exit port 306 includes a small conical tip 308 protruding from the lower surface of the frame 282. The small tip 308 either limits or prevents small drops from forming on and adhering to (i.e., hanging on to) the lower surface of the frame 282.

The fluid cartridge assembly 224 may include a bar code or a data key, for example, containing identification related to the fluid contents in the wells 264 so that the IHC tissue processing system 222 can create a processing protocol (e.g., processing temperature, processing times, fluid volumes, etc.) based upon the information. The control unit of the IHC tissue processing system 222 may include a sensor for reading the information on the bar code or the data key.

Figure 38:
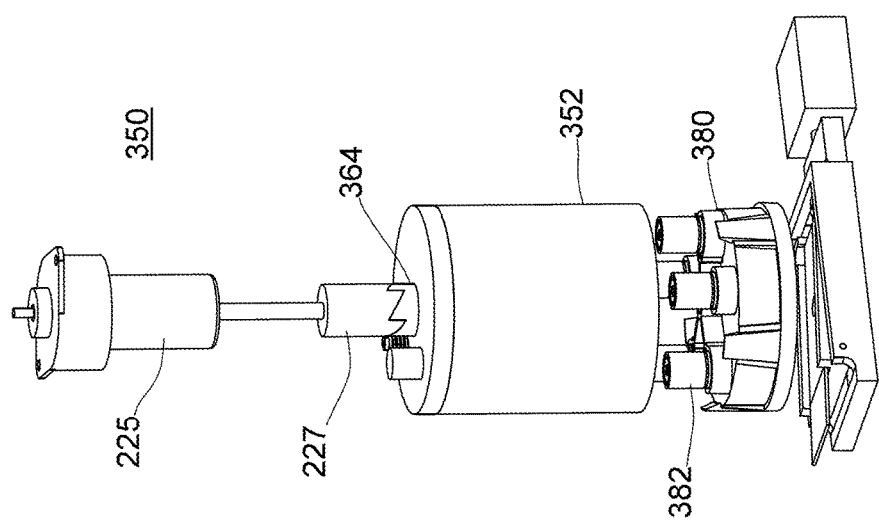
FIG. 38 is a perspective view of yet another IHC tissue processing system.

The fluid cartridge assembly 224 may vary from that which is shown and described. For example, the number, size and position of the wells 264 may vary. The wells 264 may have different sizes for containing different volumes of fluid. Alternative fluid cartridge assemblies are shown in FIGS. 36 and 38, which are configured for use with different IHC tissue processing systems.

Referring still to the features of the IHC tissue processing system 222, the slide 223 is positioned in a cradle 323 that is rotatably mounted in a carrier 320 by one or more pins 322. A linear actuator 324 is mounted adjacent the carrier 320. A driver 326 is mounted to the translating shaft of the actuator 324, and the actuator 324 is configured to translate the driver 326 back and forth with respect to the slide 223. The driver 326 is positioned beneath one end of the cradle 323. Moving the driver 326 towards the slide 223 causes the cradle 323 to pivot about the pin 322 to a horizontal state (not shown). Moving the driver 326 in the opposite direction away from the slide 223 causes the cradle 323 (and the slide 223 positioned thereon) to pivot about the pin 322 to a slanted state (shown in FIGS. 27 and 28), which causes fluid to roll off of the slide 223 under the force of gravity. A heater 325 is connected to the cradle 323 for heating the slide 223.

Referring now to the operation of the IHC tissue processing system 222, the control unit senses the rotational position of the piston driver 250 using the sensor 278. If the piston driver 250 is not in the proper rotational position, then the linear actuator 225 is operated to cause the ratchet driver 227 to rotate (but not translate) the piston driver 250, thereby preventing the pistons 260 from engaging the wells 264 and expelling fluid therefrom, until the piston driver 250 is moved to the proper rotational position. This is referred to as the "rotational alignment step."

To rotate the piston driver 250 to the proper rotational position, the linear actuator 225 causes the ratchet driver 227 to translate in a downward direction "D" (see FIG. 27) by a first distance, which causes the tooth tips 271 of the driver 227 to bear on the angled surfaces 255 of the driver 252. The upward biasing force of the spring 240 causes the driver 252 (along with the entire piston driver 250) to rotate in a clockwise direction as the tooth tips 271 of the driver 227 slide downward along the angled surfaces 255 of the driver 252. The driver 252 is initially rotated against the holding force of the spring-loaded bearing 268 in a first depression 266 (the bearing 268 is initially in the position shown in FIG. 29B). In other words, rotation of the driver 252 causes the bearing 268 to withdrawal upwardly into its sleeve 270 and separate from the first depression 266. It should be understood that the driver 227 does not rotate as it translates downward. The driver 252 rotates in the clockwise direction until the tooth tips 271 of the driver 227 are positioned within the interior corners 273 of the driver 252, and vice versa. At this time, the pistons 260 are radially aligned with two openings 236 in the bottom side of the cylinder 234.

Once the piston driver 250 is in the proper rotational position, the linear actuator 225 again causes the ratchet driver 227 to translate in a downward direction "D" (see FIG. 27) by the first distance, which causes the tooth tips 271 of the driver 227 to bear on the angled surfaces 255 of the driver 252. The upward biasing force of the spring 240 causes the driver 252 (along with the entire piston driver 250) to rotate in a clockwise direction as the tooth tips 271 of the driver 227 slide downward along the angled surfaces 255 of the driver 252. The driver 252 is initially rotated against the holding force of the spring-loaded bearing 268 in a first depression 266 (the bearing 268 is initially in the position shown in FIG. 29B). The driver 252 rotates in the clockwise direction until the tooth tips 271 of the driver 227 are positioned within the interior corners 273 of the driver 252, and vice versa.

At this time, the pistons 260 are radially aligned with two openings 236 in the bottom side of the cylinder 234. Also, as a result of the above-described rotation of the piston driver 250, the above-described first depression 266 is now radially separated from the spring-loaded ball 268, however, a second depression 266 that is adjacent the first depression 266 is now nearly aligned with the spring-loaded ball 268, as shown in FIG. 29A.

Further translation of the driver 227 in the downward direction along a second distance, which is greater than the first distance, causes the driver 227 to translate the driver 252 (along with the entire piston driver 250) in the downward direction against the bias of the spring 240. This causes the wall 251 of the piston driver 250 to separate from the underside of the cover 235. At the same time, the pistons 260 of the piston driver 250 pass through said two openings 236 in the bottom side of the cylinder 234 and contact the top ends of one or more pins 262 that are positioned within the wells 264. The number of pins 262 (i.e., either one or two) that are depressed by the pistons 260 depends upon the rotational position of the piston driver 250 with respect to well 264'.

Further translation of the driver 227 along the second distance causes the pistons 260 to translate the pin(s) 262 downward so that they pierce their membranes and deliver fluid from their wells 264 into the fluid passageway(s) of the fluid cartridge assembly 224. The driver 227 is moved downward until the pin(s) 262 are completely depressed in their respective wells 264. Alternatively, depending upon the rotational position of the piston driver 250, one of the pistons 260 may translate freely in the gap 265 between two adjacent wells 264.

As the pin(s) 262 move downwardly, the fluid stored in each well 264 passes through the vertical passage 300 formed in the frame 280, then through the hole 302 in the seal 286, then into the elongated slot 304 (and/or slot 304' and 304") formed on the top surface of the frame 282, then through the exit port 306 of the frame 282, and onto the top face of the slide 223. The slide 223 may be maintained in the horizontal position so that the fluid resides on and permeates the tissue sample on the slide 223.

After the driver 227 has moved downward to its full extent (i.e., the full second distance) and the pin(s) 262 are completely depressed inside their well(s) 264, the linear actuator 225 retracts the driver 227 in an upward direction (and without rotation) such that the teeth of the driver 227 are positioned above the teeth of the driver 252. At the same time, the spring 240 is permitted to expand and move the piston driver 250 in the upward direction until the wall 251 of the piston driver 250 contacts the underside of the cover 235. The spring loaded ball 268 then moves from the position shown in FIG. 29A to the position shown in FIG. 29B as the spring loaded ball 268 springs into the second depression 266. The force of the spring-loaded ball 268 causes the piston driver 250 to rotate by a slight degree in the clockwise direction such that the tooth tips 271 of the ratchet driver 227 are now radially aligned with respective angled surfaces 255 of the ratchet driver 252, as shown in FIG. 29B. Accordingly, the ratchet driver 227 can again cause rotation and translation of the piston driver 250 when the process is repeated.

After a pre-determined amount of time, the control unit (not shown) activates the heater 325 to heat the slide 223. The control unit then instructs the linear actuator 324 to move the driver 326 away from the slide 223, thereby causing the slide 223 to pivot about the pin 322 to a slanted state (shown in FIGS. 27 and 28). Pivoting the slide 223 causes the fluid to roll off of the slide 223 under the force of gravity and into a waste receptacle (not shown).

The above-described process is repeated until the fluid that is contained inside all of the wells 264 is emptied onto the slide 223. It should be understood that the operation of only one station of the tissue processing system 222 has been described, however, this process may be the same for the other stations of the tissue processing system 222 and processing for all of the stations can be performed simultaneously.

Figure 35:
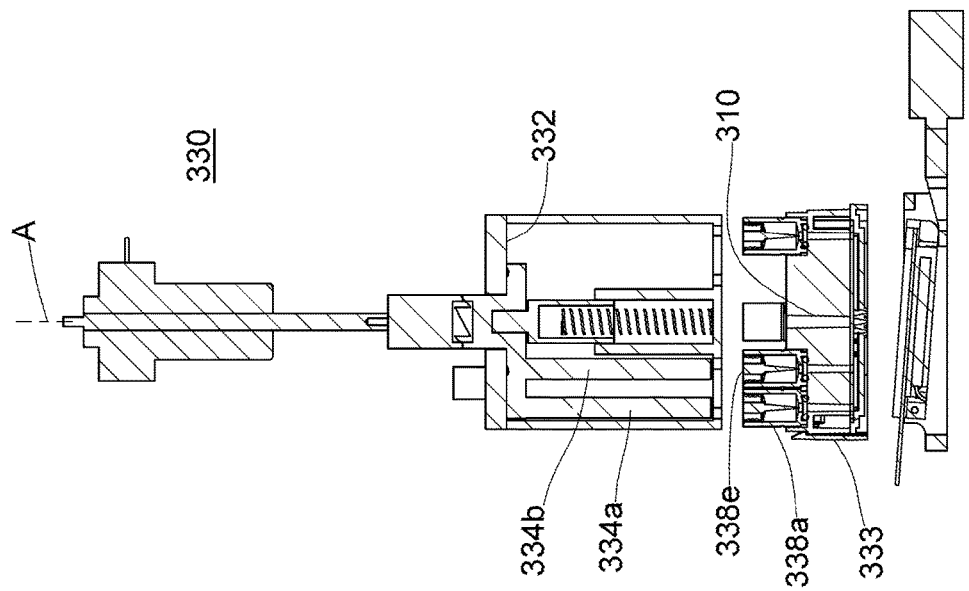
FIG. 35 is a cross-sectional view of the IHC tissue processing system of FIG. 34.
Figure 34:
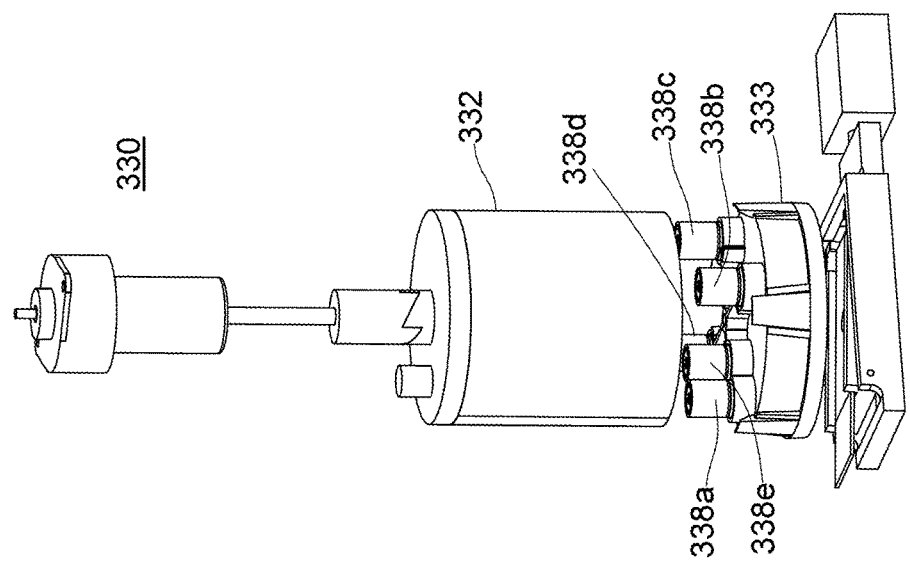
FIG. 34 is a perspective view of another IHC tissue processing system.

FIGS. 34 and 35 depict perspective and cross-sectional views of an IHC tissue processing system 330 for processing a laboratory slide. The IHC tissue processing system 330 is substantially similar to the IHC tissue processing system 222 of FIGS. 27 and 28, and only the differences between those IHC tissue processing systems will be described hereinafter.

The piston driver 332 of the tissue processing apparatus 330 includes two pistons comprising an outer piston 334a and an inner piston 334b (referred to collectively as pistons 334). The pistons 334a and 334b are radially aligned with respect to the longitudinal axis 'A' of the piston carriage. The outer piston 334a is spaced a greater distance from the longitudinal axis 'A' than the inner piston 334b.

The fluid cartridge assembly 333 includes five wells 338a-338e (referred to collectively as wells 338). Four of the outermost wells, i.e., wells 338a-338d, are oriented along an imaginary circle having a center axis that is co-aligned with the longitudinal axis 'A.' The outer wells 338a-338d are evenly spaced apart along the circle by 90 degrees. An inner well 338e is radially aligned with well 338a, however, it is not co-aligned along the imaginary circle with the outer wells 338a-338d. The well 338a is spaced a greater distance from the longitudinal axis 'A' than the inner well 338e. The distance separating the wells 338a and 338e is the same as the distance separating the pistons 334a and 334b.

The well 338e is positioned such that when the outer piston 334a is positioned within well 338a, the inner piston 334b is concurrently positioned within well 338e. The arrangement of the pistons 334a and 334b and the wells 338a and 338e makes it possible to simultaneously deliver fluid from the wells 338a and 338e into a combined channel 335 of the internal fluid passageway of the fluid cartridge assembly 333 and onto the slide. When the outer piston 334a is positioned in one of the other outer wells 338b-338d, the inner piston 334b is not positioned within any well. The structure of each well 338 is substantially identical to the wells 158 of FIG. 25.

Figure 37:
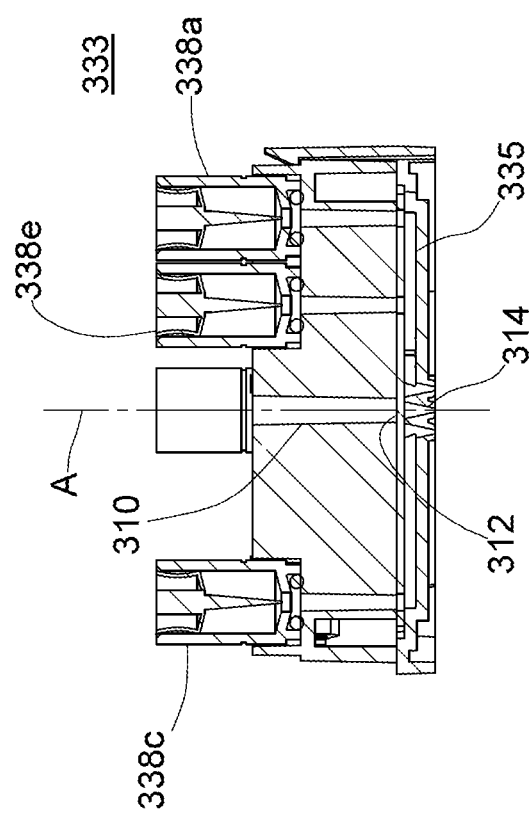
FIG. 37 is a cross-sectional view of the cartridge assembly of FIG. 36 taken along the lines 37-37.

As best shown in FIGS. 36 and 37, the fluid cartridge assembly 333 also provides a bypass passageway for injecting fluid into the fluid cartridge assembly 333 without using a well 338. The bypass passageway includes a through-hole 310 formed in the center of the upper frame, which connects to a hole 312 in the seal, which connects to a frusto-conically shaped exit port 314 formed in the center of the lower frame, through which the fluid exits the fluid cartridge assembly 333 and is directed onto the slide.

Although not shown, in operation of the IHC tissue processing system 330, a pump (not shown) delivers fluid through a conduit (not shown) that is connected to the above-described bypass passageway of the fluid cartridge assembly 333. Fluid is delivered through the conduit, into the through-hole 310 of the upper frame, through the hole 312 in the seal, through the exit port 314 of the frame, and onto the slide.

Figure 39:
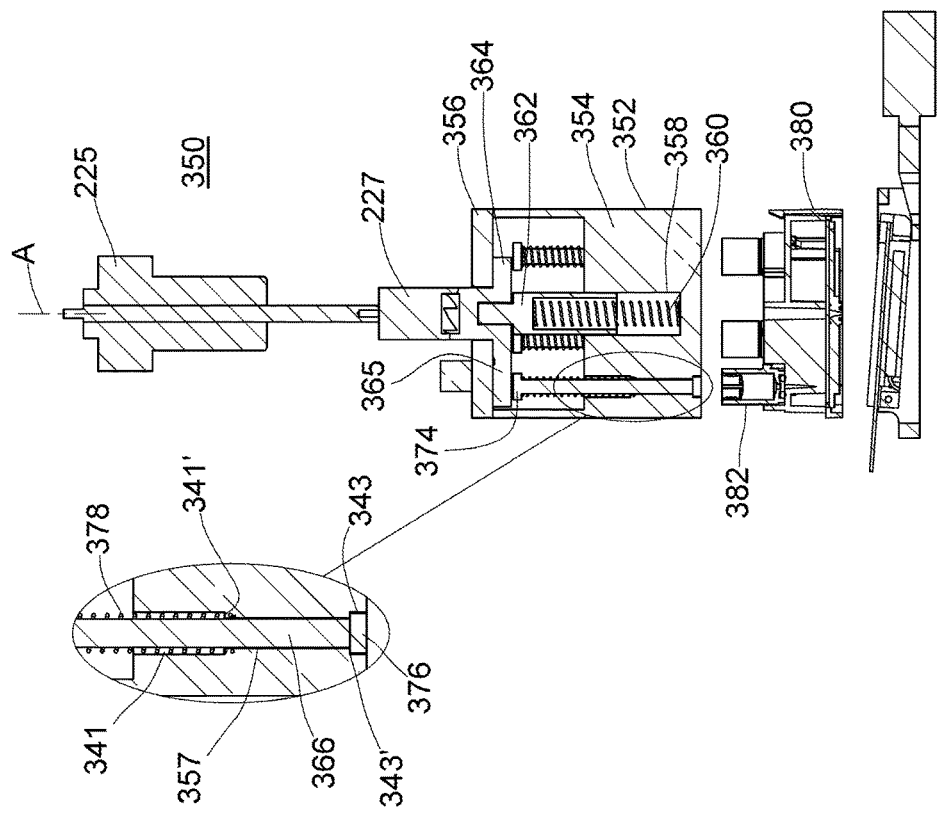
FIG. 39 is a cross-sectional view of the IHC tissue processing system of FIG. 38.

FIGS. 38 and 39 depict perspective and cross-sectional views of another IHC tissue processing system 350 for processing a laboratory slide. The IHC tissue processing system 350 is substantially similar to the IHC tissue processing systems 222 of FIGS. 27 and 28, and only the differences between those IHC tissue processing systems will be described hereinafter. Unlike the IHC tissue processing systems 222 and 330, the pistons 370a-370e (referred to collectively as pistons 370) do not rotate along with a piston driver 364, rather, the piston driver 364 selectively depresses different pistons 370 as it rotates and then translates.

As best shown in FIG. 40, the piston carriage 352 includes a cup-shaped cylinder 354 having an open top end, which is enclosed by a cover 356, and a substantially solid base extending vertically between a planar interior surface 349 and a bottom end 347. A series of five stepped thru-holes 357a-357e are formed through the solid base of the cylinder 354. The thru-holes 357a-357e are uniformly spaced apart along an imaginary circle having a center axis that is co-aligned with the longitudinal axis 'A.'

Three of the holes, i.e., holes 357a-357c, each have an enlarged counterbore 341 extending downward from the planar interior surface 349 of the cylinder 354, and another enlarged counterbore 343 extending upward from the bottom end 347 of the cylinder 354. A shoulder 341' is formed at the base of the counterbore 341, and, similarly, a shoulder 343' is also formed at the base of the counterbore 343. Two of the thru-holes, i.e., holes 357d and 357e, each have an enlarged counterbore 345 extending upward from the bottom end 347 of the cylinder 354. A shoulder 345' is formed at the base of the counterbore 345.

A blind central hole 358 is defined in the center of the solid bottom end and is aligned with longitudinal axis 'A.' A compression spring 360 is positioned within the interior of the blind central hole 358 for biasing a sliding member 362 and the piston driver 364 in an upward vertical direction (like the spring 240 biases the sliding member 242 and the piston driver 250 of FIG. 28). Another blind hole 359 (see the cross-sectional view of FIG. 40) is defined on the imaginary circle between two adjacent stepped thru-holes 357. A spring 361 is positioned within the interior of the hole 359 for biasing a bar 372 that is connected to two pistons 370d and 370e in an upward vertical direction.

Figure 41:
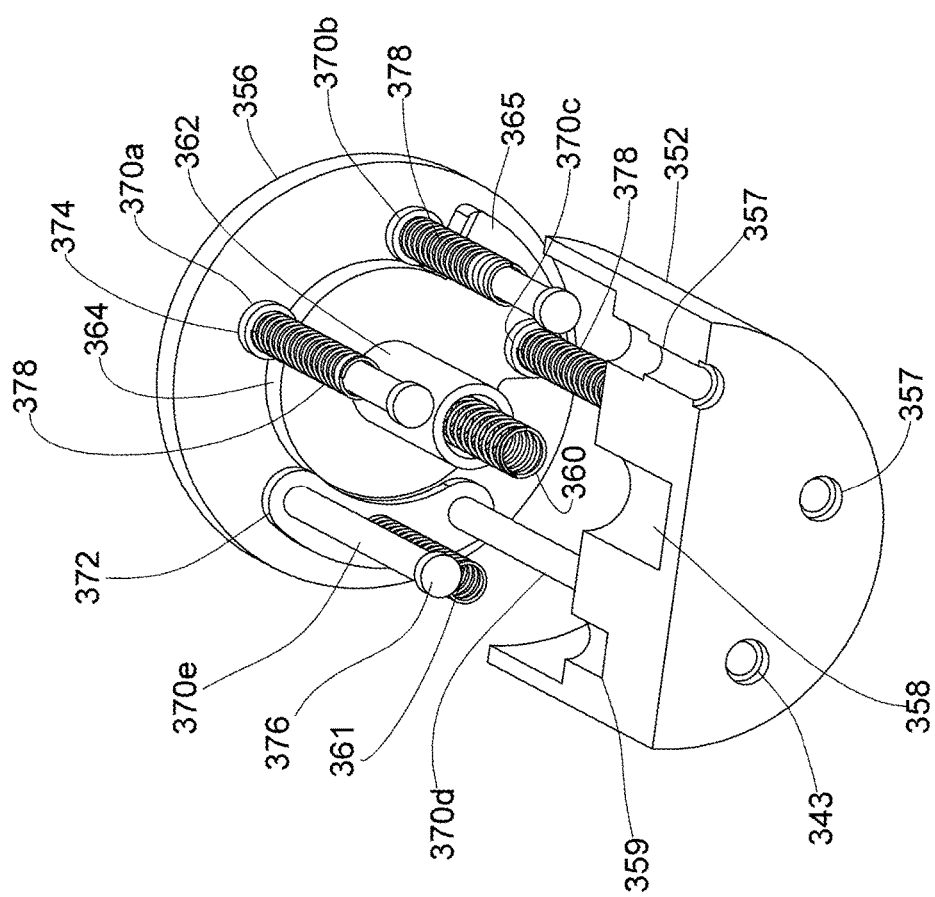
FIG. 41 depicts an exploded view taken from the bottom side of the piston carriage of the IHC tissue processing system of FIG. 38, wherein the cylinder of the piston carriage is partially cut away to reveal the stepped holes.
Figure 42:
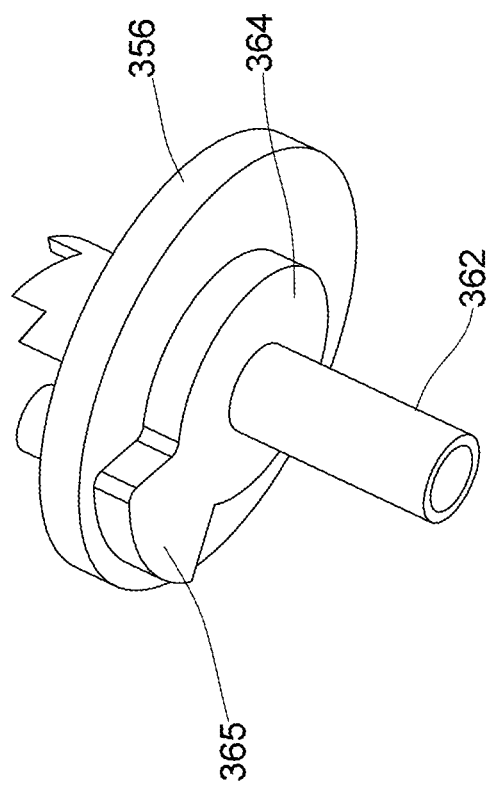
FIG. 42 depicts an assembly view taken from the bottom side of the piston carriage of the IHC tissue processing system of FIG. 38.

FIGS. 40-42 depict partial assembly views of the piston carriage 352 of the system 350. The piston driver 364 of the piston carriage 352 includes a circular wall 367, and an integral driving surface 365 that extends radially outward from the circular wall 367 and across a portion of the circumference of the circular wall 367. The driving surface 365 is configured to selectively translate and depress the individual pistons 370a-370e in a downward vertical direction. As noted above, unlike the piston driver 250 of FIG. 28, the pistons 370 are detached from the piston driver 364 and the pistons 370 do not rotate along with the piston driver 364.

Each piston 370a-370e is captively positioned in one of the five stepped thru-holes 357a-357e, respectively. Unlike the pistons 260 of FIG. 27, each piston 370a-370e is captivated, and, thus dedicated, to the same hole 357a-357e, respectively. Three of the pistons 370a-370c each includes a cylindrical shaft, an enlarged cylindrical abutment 374 defined at the top end of the shaft, and an enlarged cylindrical abutment 376 defined at the bottom end of the shaft. The enlarged cylindrical abutments 374 and 376 have a diameter that is greater than that of the cylindrical shaft.

In an assembled form of the piston carriage 352, the pistons 370a-370c are positioned in stepped thru-holes 357a-357c, respectively. A spring 378 is positioned about the shaft of each piston 370a-370c. The top enlarged cylindrical abutment 374 of each piston 370-370c is moveably positioned in the top counterbore 341. A spring 378 is mounted in the top of each counterbore 341 between the shoulder 341' of the counterbore 341 and the underside of the top enlarged cylindrical abutment 374 of each piston 370-370c. Each spring 378 biases one of the pistons 370-370c in an upward vertical direction. The bottom cylindrical abutment 376 of each piston 370a-370c is moveably positioned in the lower counterbore 343. Each spring 378 also biases the bottom cylindrical abutment 376 of the pistons 370a-370c in an upward vertical direction to bear on the shoulder 343' of the respective counterbores 343. Each piston 370a-370c is captivated in the holes 357a-357c between the shoulders 341' and 343' of each hole 357a-357c, respectively.

The top end of the pistons 370d and 370e are connected by a bar 372 to form an integral unit. In operation, the bar 372 is configured to be contacted by the piston driver 365 so that the pistons 370d and 370e translate simultaneously, and can enter two adjacent wells 382 at the same time. The pistons 370d and 370e are positioned in stepped thru-holes 357d and 357e, respectively. The bottom cylindrical abutment 376 of each piston 370d and 370e is moveably positioned in a respective lower counterbore 343 of the thru-holes 357d and 357e. The spring 361, which is positioned in a separate hole 359 and bears on the underside of bar 372, simultaneously biases both pistons 370d and 370e in an upward vertical direction such that the bottom cylindrical abutment 376 of each pistons 370d and 370e bears on the shoulder 343' of the respective counterbores 343.

The fluid cartridge assembly 380 includes five wells 382 that correspond in location to the five pistons 370. The wells 382 are the same as the above-described wells including a pin. The wells 382 are evenly arranged about a single imaginary circle having a center that is co-aligned with the longitudinal axis 'A,' and the wells 382 are each separated by 72 degrees about that circle. The fluid cartridge assembly 380 of the IHC tissue processing system 350 includes the same bypass passageway that was described with reference to the fluid cartridge assembly 333.

In operation, the linear actuator 225 causes the ratchet driver 227 to translate in a downward direction "D," which causes the piston driver 364 to initially rotate by 72 degrees (as previously described with reference to FIGS. 29A and 29B). Further translation of the ratchet driver 227 in the downward direction causes the driver 227 to translate the piston driver 364 in the downward direction against the bias of the spring 360. This causes the piston driver 364 to separate from the underside of the cover 356. At the same time, the underside of the driving surface 365 of the piston driver 364 physically contacts either (i) the bar 372 of pistons 370d and 370e, or (ii) the top surface of only one of the top enlarged cylindrical abutments 374 of the pistons 370a-370c, depending upon the rotational position of the piston driver 364.

When the underside of the driving surface 365 of the piston driver 364 physically contacts the bar 372 of pistons 370d and 370e, for example, both pistons 370d and 370e simultaneously translate in the downward vertical direction against the bias of spring 361 and the bottom enlarged cylindrical abutment 376 of the pistons 370d and 370e enter their respective wells 382. The pistons 370d and 370e depress the pins in their respective wells 382 to simultaneously expel fluid from those wells and onto the slide, as previously described. Due to the vertical space between the driving surface 365 and the underside of the cover 356, the driver 364 does not contact any of the remaining pistons 370a-370c as the driving surface 365 is moving in a downward vertical direction.

The actuator 225 then causes the ratchet driver 227 to translate in an upward vertical direction, and the spring 360 moves the piston driver 364 upwardly against the cover 356 to its starting position. At the same time, the spring 361 moves the pistons 370d and 370e upwardly to their starting positions.

The actuator 225 then causes the ratchet driver 227 to translate in a downward vertical direction, which causes the piston driver 364 to initially rotate by another 72 degrees (as previously described with reference to FIGS. 29A and 29B) such that the driving surface 365 of the piston driver 364 is radially aligned with piston 370a. Further translation of the ratchet driver 227 in the downward direction causes the driver 227 to translate the piston driver 364 in the downward direction against the bias of the spring 360. This causes the piston driver 364 to separate from the underside of the cover 356. The driving surface 365 of the piston driver 364 moves downward and physically contacts the top surface of the top enlarged cylindrical abutment 374 of the piston 370a. The piston 370a is translated in the downward vertical direction against the bias of its own spring 378. The bottom enlarged cylindrical abutment 376 of the piston 370a then enters its well 382, thereby expelling fluid from the well and onto the slide as previously described. Again, due to the vertical space between the driving surface 365 and the underside of the cover 356, the driver 364 does not contact any of the remaining pistons 370b-370e as the driving surface 365 is moving in a downward vertical direction. This process is repeated as needed or until all of the wells 382 are emptied of their contents.

Figure 43A:
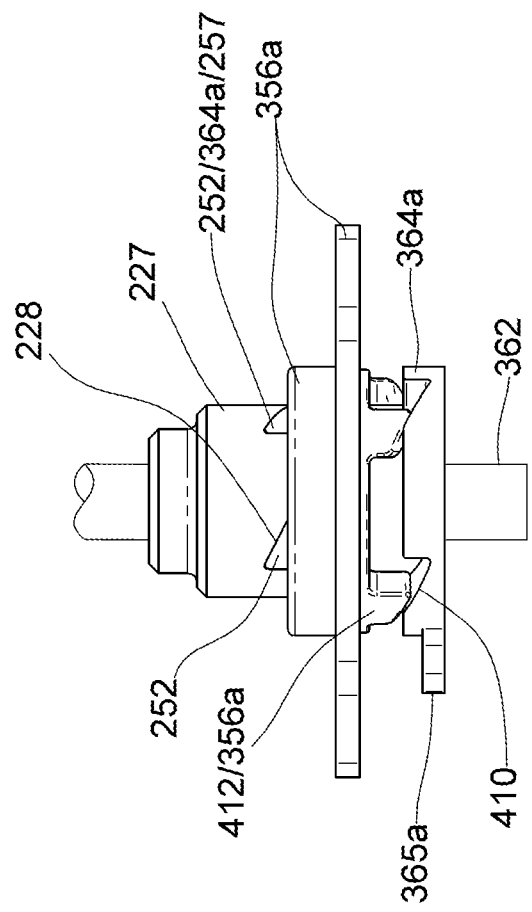
FIGS. 43A and 43B depict partial assembly views showing an alternative arrangement of the mating drivers of the IHC tissue processing system of FIG. 27, wherein the drivers are shown in the engaged and disengaged positions, respectively.
Figure 43B:
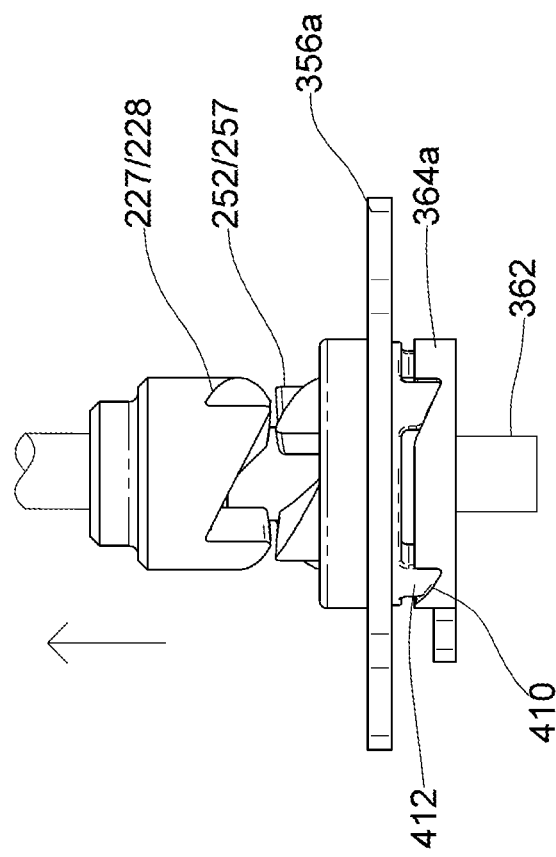

FIGS. 43A and 43B depict an alternative to the arrangement of the ball 268 and the depressions 266 of the system 350 for auto-rotating the driver 252 of the piston driver 364a to the proper position after each reciprocating translational motion of the driver 227.

As applied to the system 350 of FIG. 38, a set of ramped surfaces 412 extend from the lower surface of the stationary cover 356a, and a mating set of ramped surfaces 410 extend upward from a central surface of the piston driver 364a. The ramped surfaces 410 and 412 are configured to mesh with each other to accomplish slight auto-rotation of the driver 252 (along with the entirety of the piston driver 364a) after each reciprocating translational motion of the driver 227, as will be explained hereinafter.

In operation, as shown in FIG. 43A, when the driver 227 is fully depressed in the downward direction, the teeth 228 and 257 of the drivers 227 and 252, respectively, are completely meshed together. At the same time, the sloped surfaces of the teeth 412 of the cover 356a are positioned on the sloped surfaces of their respective teeth 410 of the piston driver 364a. The teeth 410 and 412 are not yet completely meshed together.

As shown in FIG. 43B, when the driver 227 is moved in the upward direction (see arrow) away from the driver 252, the spring (not shown) within the sliding member 362 causes the sliding member 362 along with the entirety of the piston driver 364a to move in the upward direction. The upward motion of the piston driver 364a causes the teeth 410 of the piston driver 364a to slide along their respective teeth 412 of the stationary cover 356a as the piston driver 364a (along with the driver 252) rotates and moves upwardly. Once the teeth 410 and 412 are completely meshed together (as shown in FIG. 43B), the driver 252 of the piston driver 364a is sufficiently rotated so that the teeth 228 of the driver 228 are now rotationally aligned with the ramped surfaces of the teeth 257 of the driver 252 for the next reciprocating motion of the driver 227.

It should be understood by those skilled in the art that the set of meshing ramped surfaces can be applied to the other IHC tissue processing systems of FIGS. 27 and 34 to achieve the same auto-rotation result.

While exemplary embodiments of the invention have been shown and described herein, it will be understood that such embodiments are provided by way of example only. Numerous variations, changes and substitutions will occur to those skilled in the art without departing from the spirit of the invention. For example, the fluid-containing wells are optional features of the invention, and may be replaced by holes through which fluid is distributed, for example. Accordingly, it is intended that the appended claims cover all such variations as fall within the spirit and scope of the invention.

What is claimed is:

1. A fluid-containing cartridge for a tissue processing apparatus comprising:

a body defining a plurality of discrete fluid passageways, and a plurality of fluid-containing wells disposed on the body, wherein each fluid passageway of the body defines a fluid path between one of the fluid-containing wells and a discrete fluid exit port, wherein each discrete fluid exit port is configured to separately dispense fluid onto a laboratory slide, the body further comprising a slide receiving area to which the laboratory slide is configured to be attached; and the laboratory slide, which is removably mounted to the slide receiving area of the body and positioned at a location adjacent the fluid exit ports to receive the fluid delivered from the fluid exit ports.

2. The fluid-containing cartridge of claim 1, wherein the fluid passageways are internal passageways defined within the body of the cartridge.

3. The fluid-containing cartridge of claim 1 further comprising a depressible pin positioned in each fluid-containing well, the fluid-containing wells containing either a reagent solution or a buffer solution.

4. A tissue processing system for processing the laboratory slide, said system comprising the fluid containing cartridge of claim 3, and a piston carriage including at least one piston for depressing the depressible pin positioned in one of the fluid-containing wells.

5. The tissue processing system of claim 4, wherein the piston carriage includes at least two pistons for simultaneously engaging two depressible pins positioned in two of the fluid-containing wells.

6. The tissue processing system of claim 5, wherein the piston carriage comprises a piston driver that is disconnected from the at least two pistons, wherein the piston driver is configured to (i) rotate to radially align a driving surface of the piston driver with one piston of the at least two pistons, (ii) translate said one piston of the at least two pistons to depress the depressible pin, and (iii) rotate to radially align the driving surface of the piston driver with the other piston of the at least two pistons.

7. The tissue processing system of claim 4, wherein the piston carriage comprises a piston driver that is configured to rotate to radially align said at least one piston with said at least one fluid-containing well, and then translate said at least one piston to depress the depressible pin.

8. The tissue processing system of claim 4, wherein the piston carriage is configured to convert (i) translation input motion by a first distance into rotation of the at least one piston without translation, and (ii) translation input motion by a second distance that is greater than the first distance into rotation and then translation of the at least one piston.

9. The fluid-containing cartridge of claim 1, wherein the body further comprises a condensation chamber for collecting vapor produced within the slide receiving area during processing of the laboratory slide and returning condensed vapor to the slide receiving area.

10. The fluid-containing cartridge of claim 9, wherein the condensation chamber includes a port exposed to atmospheric pressure.

11. The fluid-containing cartridge of claim 10 further comprising a fluid entrance passageway extending between the slide receiving area and the condensation chamber through which the vapor is transported to the condensation chamber, and a separate fluid exit passageway extending between the condensation chamber and the slide receiving area through which condensed vapor returns to the slide receiving area.

12. The fluid-containing cartridge of claim 1, wherein the body comprises a first body portion to which the plurality of fluid-containing wells are mounted, and a second body portion including the slide receiving area, wherein the first body and the second body are releasably connected together.

13. The fluid-containing cartridge of claim 1 further comprising a connector for connecting the slide to the slide receiving area of the cartridge.

14. The fluid-containing cartridge of claim 1 further comprising a gasket positioned in the slide receiving area between the slide and a body of the cartridge, wherein the fluid is delivered to an area that is circumscribed by the gasket.

15. The fluid-containing cartridge of claim 1, wherein the cartridge further comprises two separate drain ports connected to the slide receiving area, through which fluid is expelled from the cartridge.

16. The fluid-containing cartridge of claim 1, wherein two additional fluid passageways merge into a single merged fluid passageway.

17. The fluid-containing cartridge of claim 16, wherein the single merged fluid passageway includes a series of protrusions for mixing together the fluid streams delivered from said two additional fluid passageways.

18. The fluid-containing cartridge of claim 1, wherein the fluid-containing wells vary in size.

19. The fluid-containing cartridge of claim 1, wherein the fluid exit port terminates at a conical tip that is configured to dispense fluid onto the slide, which is positioned beneath the conical tip of the fluid-containing cartridge.

20. The fluid-containing cartridge of claim 1, wherein at least one of the plurality of fluid-containing wells mounted to the body is a fluid-containing well that is positioned within a hollow well that is disposed on the body.

21. A fluid-containing cartridge for a tissue processing apparatus comprising:
a body defining a plurality of discrete fluid passageways,
a plurality of fluid-containing wells disposed on the body, the fluid-containing wells containing either a reagent solution or a buffer solution, wherein each fluid passageway of the body defines a fluid path between one of the fluid-containing wells and a fluid exit port that is configured to dispense fluid onto a laboratory slide;
a depressible pin positioned in each fluid-containing well, each depressible pin including (i) a sealing portion that is configured to seal against a perimeter of an interior wall of the well as the depressible pin translates along the interior wall, and (ii) a sharp tip extending from the sealing portion; and
a puncturable membrane disposed at a lower end of each well that is configured to be punctured by the sharp tip of the depressible pin that is located in the well as the depressible pin translates along the interior wall of the well.

22. A tissue processing system for processing the laboratory slide, said system comprising the fluid containing cartridge of claim 21, and a piston carriage including at least one piston for depressing the depressible pin positioned in one of the fluid-containing wells.

23. The tissue processing system of claim 22, wherein the piston carriage includes at least two pistons for simultaneously engaging two depressible pins positioned in two of the fluid-containing wells.

24. The fluid-containing cartridge of claim 21, wherein the body comprises a first body portion to which the plurality of fluid-containing wells are mounted, and a second body portion including a slide receiving area, wherein the first body and the second body are releasably connected together.

25. The fluid-containing cartridge of claim 21, wherein two additional fluid passageways merge into a single merged fluid passageway.

26. The fluid-containing cartridge of claim 25, wherein the single merged fluid passageway includes a series of protrusions for mixing together the fluid streams delivered from said two additional fluid passageways.

27. A cartridge for a tissue processing apparatus comprising:
a body defining a plurality of discrete fluid passageways, each fluid passageway defining a fluid path through which processing fluid passes to one or more fluid exit ports defined in the body, and a slide receiving area defined on the body upon which a laboratory slide is mountable, the slide receiving area being circumscribed by a gasket disposed between the laboratory slide and the body, the slide receiving area being positioned to receive the processing fluid from the one or more fluid exit ports of the discrete fluid passageways in order to expose the laboratory slide to the processing fluid.

28. The cartridge of claim 27, wherein the condensation chamber is defined above the slide receiving area for collecting vapor produced during processing of the slide.

29. The cartridge of claim 27, wherein the condensation chamber includes a port exposed to atmospheric pressure.

30. The cartridge of claim 27 further comprising a fluid entrance passageway extending between the slide receiving area and the condensation chamber through which the vapor is transported to the condensation chamber, and a separate fluid exit passageway extending between the condensation chamber and the slide receiving area through which condensed vapor returns to the slide receiving area.

* * * * *